(12) United States Patent
Watanabe et al.

(10) Patent No.: US 11,744,830 B2
(45) Date of Patent: Sep. 5, 2023

(54) AMELIORATIVE AGENT FOR CYTOKINE RELEASE SYNDROME AND SO ON

(71) Applicant: TORII PHARMACEUTICAL CO., LTD., Tokyo (JP)

(72) Inventors: Yoshihiro Watanabe, Tokyo (JP); Yoshio Tahara, Tokyo (JP); Keisuke Suzuki, Tokyo (JP); Takayuki Mimura, Tokyo (JP); Saori Ohmae, Tokyo (JP)

(73) Assignee: TORII PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 17/053,179

(22) PCT Filed: Nov. 29, 2019

(86) PCT No.: PCT/JP2019/046689
§ 371 (c)(1),
(2) Date: Nov. 5, 2020

(87) PCT Pub. No.: WO2020/111212
PCT Pub. Date: Jun. 4, 2020

(65) Prior Publication Data
US 2021/0128550 A1    May 6, 2021

(30) Foreign Application Priority Data

Nov. 29, 2018  (JP) ................... 2018-223377
Sep. 11, 2019  (JP) ................... 2019-165013

(51) Int. Cl.
*A61K 31/495*    (2006.01)
*A61P 37/06*    (2006.01)

(52) U.S. Cl.
CPC ............ *A61K 31/495* (2013.01); *A61P 37/06* (2018.01)

(58) Field of Classification Search
CPC .................................................. A61K 31/495
See application file for complete search history.

(56) References Cited

U.S. PATENT DOCUMENTS

| 6,174,887 B1 | 1/2001 | Haruta et al. | |
| 2009/0131329 A1* | 5/2009 | Miller ................... | A61K 45/06 514/1.1 |

FOREIGN PATENT DOCUMENTS

WO    WO 97/08133 A1    3/1997

OTHER PUBLICATIONS

Tajima et al., JTE-607, a multiple cytokine production inhibitor, induces apoptosis accompanied by an increase in p21waf1/cip1 in acute myelogenous leukemia cells, Cancer Sci., Mar. 2010; 101(3): 774-81.*
Kakatani et al., JTE-607, a novel inflammatory cytokine synthesis inhibitor without immunosuppression, protects from endotoxin shock in mice, Inflammation Research vol. 48, pp. 461-468(1999).*
Lee, Current concepts in the diagnosis and management of cytokine release syndrome, Blood, Jul. 10, 2014, as4 (2): 188-195.*
Giaviridis et al., CAR T cell-induced cytokine release syndrome is mediated by macrophages and abated by IL-1 blockade, Nat Med, Jun. 2018;24(6):731-738.*
Ferra et al., IL-6 and IL-8 levels in plasma during hematopoietic progenitor transplantation, Haematologica, Dec. 1998;83(12):1082-7 (Abstract).*
Bracaglia et al., Macrophage Activation Syndrome: different mechanisms leading to a one clinical syndrome, Pediatr Rheumatol Online J. 2017; 15:5.*
Brisse et al., Hemophagocytic lymphohistiocytosis (HLH): A heterogeneous spectrum of cytokine-driven immune disorders, Cytokine & Growth Factor Reviews, vol. 26, Issue 3, Jun. 2015, pp. 263-280.*
Murakami et al., Interleukin-1 loop model for pathogenesis of Langerhans cell histiocytosis, Cell Communication and Signaling vol. 13, Article No. 13 (2015).*
Ferreros et al., Interleukin Inhibitors in Cytokine Release Syndrome and Neurotoxicity Secondary to CAR-T Therapy, Diseases. Sep. 2022; 10(3): 41, available at https://www.ncbi.nlm.nih.gov/pmc/articles/PMC9326641/.*
Abboud et al., "Severe Cytokine Release Syndrome Following T-cell Replete Peripheral Blood Haploidentical Donor Transplant is Associated with Poor Survival and Anti-IL-6 Therapy is Safe and Well Tolerated", Biol Blood Marrow Transplant, Oct. 2016, vol. 22, No. 10, p. 1851-1860.

(Continued)

*Primary Examiner* — Svetlana M Ivanova
(74) *Attorney, Agent, or Firm* — Birch, Stewart, Kolasch & Birch, LLP

(57) ABSTRACT

[Problem to be Solved] The present invention provides a medicament for cytokine release syndrome, autoimmune-related adverse events, macrophage activation syndrome, hemophagocytic lymphohistiocytosis or Langerhans cell histiocytosis.

[Means to Solve the Problem] The present invention provides a medicament for at least one selected from the group consisting of cytokine release syndrome, autoimmune-related adverse events, macrophage activation syndrome, hemophagocytic lymphohistiocytosis and Langerhans cell histiocytosis, wherein the medicament comprises a compound represented by the following formula I:

[Formula 17]

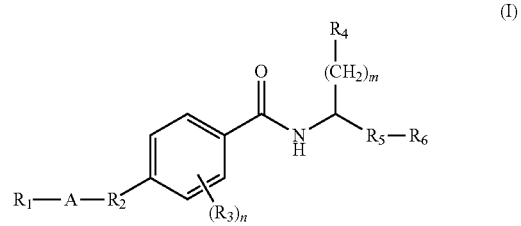

or a pharmaceutically acceptable salt thereof.

4 Claims, 20 Drawing Sheets

Specification includes a Sequence Listing.

(56) References Cited

OTHER PUBLICATIONS

Gay et al., "Immuno-oncologic Approaches: CAR-T Cells and Checkpoint Inhibitors", Clinical Lymphoma, Myeloma & Leukemia, Aug. 2017, vol. 17, No. 8, p. 471-478.
Giavridis et al., "CAR T cell-induced cytokine release syndrome is mediated by macrophages and abated by IL-1 blockade", Nature Medicine, Jun. 2018, vol. 24, No. 6, p. 731-738, total 9 pages.
International Search Report, issued in PCT/JP2019/046689, PCT/ISA/210, dated Mar. 3, 2020.
Kagoya et al., "A novel chimeric antigen receptor containing a JAK-STAT signaling domain mediates superior antitumor effects", Nat Med., Mar. 2018, vol. 24, No. 3, p. 352-359, total 20 pages.
Kakutani et al., "JTE-607, a novel inflammatory cytokine synthesis inhibitor without immunosuppression, protects from endotoxin shock in mice", Inflammation Research, 1999, vol. 48, No. 8, p. 461-468.
Kroschinsky et al., "New drugs, new toxicities: severe side effects of modern targeted and immunotherapy of cancer and their management", Critical Care, 2017, vol. 21, No. 89, p. 1-11.
Lee et al., "Current concepts in the diagnosis and management of cytokine release syndrome", Blood, Jul. 10, 2014, vol. 124, No. 2, p. 188-195.
Naidoo et al., "Toxicities of the anti-PD-1 and anti-PD-L1 immune checkpoint antibodies", Annals of Oncology 26, Sep. 14, 2015, p. 2375-2391.
Noreili et al., "Monocyte-derived IL-1 and IL-6 are differentially required for cytokine-release syndrome and neurotoxicity due to CAR T cells", Nature Medicine, Jun. 2018, vol. 24, No. 6, p. 739-748.
Ruella M et al., "Kinase inhibitor ibrutinib to prevent cytokine-release syndrome after anti-CD19 chimeric antigen receptor T cells for B-cell neoplasms", Leukemia, Jan. 2017, vol. 31, No. 1, p. 246-248.
Stroud et al., "Tocilizumab for the management of immune mediated adverse events secondary to PD-I blockade", Journal of Oncology Pharmacy Practice, Jan. 1, 2017, vol. 25, No. 3, p. 551-557.
Tajima et al., "JTE-607, a multiple cytokine production inhibitor, induces apoptosis accompanied by an increase in p21 waf1/cip1 in acute myelogenous leukemia cells", Cancer Sci. Mar. 2010, vol. 101, No. 3, p. 774-781.
Wang et al., "Immune-Related Adverse Events Associated with Anti-PD-1/PD-L1 Treatment for Malignancies: A Meta-Analysis", Frontiers in Pharmacology, Oct. 18, 2017, vol. 8, Article 730, p. 1-12.
Written Opinion of the International Searching Authority, issued in PCT/JP2019/046689, PCT/ISA/237, dated Mar. 3, 2020.
Zhang et al., "A new insight in chimeric antigen receptor-engineered T cells for cancer immunotherapy", Journal of Hematology & Oncology, Jan. 3, 2017, vol. 10, No. 1, p. 1-11.
European Patent Office Search Report dated Jun. 11, 2021 for corresponding EP Application No. 19889164.0.
Fang et al., "Pyroptosis: A new frontier in cancer"; Biomedicine & Pharmacotherapy, vol. 121, 2020, 7 pages.
Sanchez-Lopez et al., "Choline uptake and metabolism modulate macrophage IL-1 B and IL-18 production", Cell Metab., vol. 29, No. 6, Jun. 2019, 36 pages.
Shimizu et al., "Tocilizumab masks the clinical symptoms of systemic juvenile idiopathic arthritis-associated macrophage activation syndrome: The diagnostic significance of interleukin-18 and interleukin-6", Cytokine, vol. 58, 2012, pp. 287-294.
Yuk et al., "Inflammasome and Mitophagy Connection in Health and Disease", International Journal of Molecular Sciences, Jul. 2020, 27 pages.
Guidance Book for the Regular Assessment of Practicing Physicians, Pediatrics (2014), pp. 404-406 (12 pages total).
Chinese Office Action for Chinese Application No. 201980028145.3, dated Mar. 25, 2022, with English translation.
European Communication pursuant to Article 94(3) EPC for European Application No. 19889164.0, dated Mar. 18, 2022.

\* cited by examiner

AMELIORATIVE AGENT FOR CYTOKINE RELEASE SYNDROME AND SO ON

TECHNICAL FIELD

The present invention relates to a prophylactic, therapeutic or ameliorative agent for cytokine release syndrome, autoimmune-related adverse events, macrophage activation syndrome, hemophagocytic lymphohistiocytosis or Langerhans cell histiocytosis.

BACKGROUND ART

In recent years, a therapy called chimeric antigen receptor (CAR)-expressing T cell (CAR-T cell) therapy or T cell receptor (TCR)-genetically engineered T cell (TCR-T cell) therapy has been attempted for cancer treatment. Moreover, this cancer treatment mediated by T cell activation has some features in common with cancer treatment using immune checkpoint inhibitors, in terms of immune system activation occurring in vivo. Cell therapy using CAR-T or TCR-T cells is an autologous T cell therapy designed such that T cells taken from a patient are genetically engineered to express targetable CAR or particular TCR and then returned into the patient's body. CAR- or TCR-expressing T cells not only have the ability to kill target-expressing tumor cells including cancer cells (killer activity), but also efficiently expand the proliferation of functional T cells as a result of being repeatedly exposed to antigens. In addition, antigens released upon disruption of the killed tumor cells will be presented to antigen-presenting cells to thereby stimulate endogenous T cells and induce their activation. Thus, once CAR-T cells have been infused into a patient, they will be engrafted and grown in the patient's body, whereby immune surveillance can be facilitated.

Moreover, an immune checkpoint inhibitor is a drug which binds to an immune checkpoint molecule or a ligand thereof to inhibit immunosuppressive signaling and thereby cancel the immune checkpoint molecule-suppressed activation of cancer cell-recognizing T cells. Major immune checkpoint inhibitors applied in clinical practice include anti-cytotoxic T-lymphocyte associated antigen 4 (CTLA-4) antibody, anti-programmed cell death-1 (PD-1) antibody, anti-programmed death-1 ligand-1 (PD-L1) antibody, etc.

With recent advances in studies, it has been indicated that abnormal activation of monocytes or macrophages and tissue damage associated therewith (also referred to as macrophage activation syndrome, MAS), bone lesions and skin lesions or systemic organ lesions, which are referred to as hemophagocytic lymphohistiocytosis (HLH), Langerhans cell histiocytosis (LCH), etc., would be caused upon activation of T cells.

CAR-T cell therapy causes a problem called cytokine release syndrome (CRS) (i.e., CRS toxicity). CRS is a condition where blood cytokine levels are significantly increased, along with fever, hypotension, hypoxia, cerebral edema, neurodegeneration, etc.

CRS toxicity will always occur upon transfer of CAR-T cells into cancer patients, and the regulation of CRS toxicity is extremely important in expanding the application or trial of CAR-T cells[4] (Non-patent Document 1).

The mechanisms by which CAR-T cells recognize and disrupt blood cancer cells or cancer tissues have been clarified, but there is a lot of uncertainty about the mechanism of CRS toxicity. The interleukin (IL)-6R antibody (tocilizumab) approved at the same time as CAR-T cell therapy can regulate CRS toxicity below the threshold of tolerance, so that the mechanism of CRS toxicity has been suggested to involve IL-6 overproduction-induced inflammatory damage in normal tissue[5] (Non-patent Document 2).

Likewise, immune checkpoint inhibitors have also been reported to cause immune enhancement referred to as auto-immune-related adverse events (irAEs) along with inflammatory immune reactions in all organs in the body including skin, digestive system, endocrine system, nervous system, etc. (Non-patent Documents 10 and 11). The principle of treatment lies in drug withdrawal and steroid administration, but prophylactic and therapeutic agents for these irAEs have now begun to be studied, and various candidates including existing drugs are deemed to be under consideration.

Against the background of the elevation of inflammatory cytokines (e.g., TNF-α, IL-18, IL-1β, MCP-1) except for those involved in the IL-6 pathway in patients with CRS toxicity resistant to tocilizumab administration and the inapplicability of antibody drugs in such patients complicated with cerebral edema, there has been a demand for the development of drugs widely applicable to CRS toxicity and novel CAR genes. For example, on the basis of an idea that CRS toxicity can be regulated by controlling excessive activation of CAR-T cells, there has been an attempt to suppress excessive activation of CAR-T cells with BTK inhibitors[6] (Non-patent Document 3) or an attempt to regulate excessive activation of CAR-T cells by integration of a "drug susceptibility suicide gene" into the CAR gene[7] (Non-patent Document 4), etc.

For suppression of CRS toxicity, these drug candidates including currently used steroids are designed with a main focus on the suppression of CAR-T cell functions, and there is a serious concern that these drug candidates will lead to the result of cancelling the cancer regression effect of CAR-T cells, although it is temporary. Since severe CRS toxicity is lethal, the application of these drug candidates is under consideration as a passive alternative.

Under present circumstances where CAR-T cell therapy is limited mainly to blood cancers and no clear successful results have been obtained in solid cancer cases, more potent CAR genes and concomitant drugs are also under consideration. For example, strategies are also attempted to further enhance killer activity and achieve its long-term maintenance, as exemplified by the development of novel chimeric antigen receptors which rely on antigen stimulation to activate cytokine signals[8] (Non-patent Document 5), combined use with PD-1/CTLA4 antibody serving as an immune checkpoint inhibitor[9] (Non-patent Document 6), etc.

In addition, an attempt to improve the access of CAR-T cells to cancer tissues by increasing the number of CAR-T cells to be transferred or by pretreatment with an anticancer agent is also regarded as a practical strategy to enhance the cancer regression effect.

As a result of such an improvement in CAR-T cell therapy, the acceptable proper regulation of CRS toxicity which concurrently occurs or always occurs[4] will be a more important problem in the future.

On the other hand, a compound referred to as JTE-607, i.e., ((−)-ethyl N-{3,5-dichloro-2-hydroxy-4-[2-(4-methylpiperazin-1-yl)ethoxy]benzoyl}-L-phenylalaninate) dihydrochloride (Patent Document 1) was designed as a drug candidate suppressing inflammatory cytokine production.

JTE-607 is a compound suppressing inflammatory cytokine production and having selectivity for myeloid lineage cells, and its phase II study was performed on patients with systemic inflammatory response syndrome (SIRS). In the later phase I study, JTE-607 was found to suppress the production of IL-6, IL-8 and other inflammatory cytokines under LPS loading and suppress the elevation of C-reactive protein (CRP) levels in a dose-dependent manner. Moreover, JTE-607 was then found to selectively suppress the autoproliferation of acute myeloid leukemia (AML) cell lines in an in vitro system[1] (Non-patent Document 7).

There are reports showing that abnormal activation of monocytes/macrophages may be involved in the development of CRS toxicity and cerebral edema in CAR-T cell therapy[2],[3] (Non-patent Documents 8 and 9). However, this is merely a "hypothesis" inferred from the findings that CRS toxicity development is synchronized with IL-6 and other inflammatory cytokine production in clinical cytokine production profiles and that tocilizumab has an ameliorative effect on CRS toxicity. The verification of this hypothesis is expected not only to recognize the characteristics of CRS toxicity and thereby facilitate the development of appropriate drugs, but also to lead to the research and development of ameliorative and/or prophylactic agents for CRS toxicity without causing CAR-T cell suppression (immunosuppression), which is a matter of concern in the steroid (prednisolone: PSL) prescription used in tocilizumab-tolerant patients.

CAR-T cells are positioned as "anticancer T effector cells for use in massive transfer into the body" which are obtained once T cells have been processed and expanded in vitro.

The overproliferation of these T effector cells is an event which also occurs endogenously, as exemplified by "overexpansion of endogenous anticancer T effector cells" caused by administration of immune checkpoint inhibitors and "overexpansion of antiviral T effector cells" induced upon virus infection and/or multiplication. These irAEs concurrently occurring upon treatment and disease development as well as abnormal macrophage activation and cytokine overproduction in HLH and MAS can be regarded as events common with CRS toxicity concurrently occurring in CAR-T cell therapy. In fact, tocilizumab has been tested for its effect on irAEs and reported to have a certain level of effect (Non-patent Document 12).

Summing up events common to these side effects and diseases, there arises a hypothesis that individual groups of cells would mutually correlate and affect each other to cause overproliferation of T effector cells and concurrently occurring abnormal activation of macrophages, etc. Thus, the elucidation of CRS toxicity and the development of therapy would lead to a new understanding of these irAEs, HLH and MAS symptoms and the development of appropriate therapeutic agents.

PRIOR ART DOCUMENTS

Patent Documents

Patent Document 1: WO97/08133 (Example 2)

Non-Patent Documents

Non-patent Document 1: Current concepts in the diagnosis and management of cytokine release syndrome. Lee D W, Gardner R, Porter D L, Louis C U, Ahmed N, Jensen M, Grupp S A, Mackall C L. Blood. 2014 Jul. 10; 124(2): 188-95.

Non-patent Document 2: Severe Cytokine-Release Syndrome after T Cell-Replete Peripheral Blood Haploidentical Donor Transplantation Is Associated with Poor Survival and Anti-IL-6 Therapy Is Safe and Well Tolerated. Abboud R, Keller J, Slade M, DiPersio J F, Westervelt P, Rettig M P, Meier S, Fehniger T A, Abboud C N, Uy G L, Vij R, Trinkaus K M, Schroeder M A, Romee R. Biol Blood Marrow Transplant. 2016 October; 22(10):1851-1860.

Non-patent Document 3: Kinase inhibitor ibrutinib to prevent cytokine-release syndrome after anti-CD19 chimeric antigen receptor T cells for B-cell neoplasms. bRuella M, Kenderian S S, Shestova O, Klichinsky M, Melenhorst J J, Wasik M A, Lacey S F, June C H, Gill S. Leukemia. 2017 January; 31(1):246-248.

Non-patent Document 4: A new insight in chimeric antigen receptor-engineered T cells for cancer immunotherapy. Zhang E, Xu H. J Hematol Oncol. 2017 Jan. 3; 10(1):1.

Non-patent Document 5: A novel chimeric antigen receptor containing a JAK-STAT signaling domain mediates superior antitumor effects. Kagoya Y, Tanaka S, Guo T, Anczurowski M, Wang C H, Saso K, Butler M O, Minden M D, Hirano N. Nat Med. 2018 March; 24(3):352-359.

Non-patent Document 6: Immuno-oncologic Approaches: CAR-T Cells and Checkpoint Inhibitors. Gay F, D'Agostino M, Giaccone L, Genuardi M, Festuccia M, Boccadoro M, Bruno B. Clin Lymphoma Myeloma Leuk. 2017 August; 17(8):471-478.

Non-patent Document 7: JTE-607, a multiple cytokine production inhibitor, induces apoptosis accompanied by an increase in p21waf1/cip1 in acute myelogenous leukemia cells. Tajima N, Fukui. K, Uesato N, Maruhashi J, Yoshida T, Watanabe Y, Tojo A. Cancer Sci. 2010 March; 101(3):774-81.

Non-patent Document 8: CAR T cell-induced cytokine release syndrome is mediated by macrophages and abated by IL-1 blockade. Giavridis T, van der Stegen S J C, Eyquem J, Hamieh M, Piersigilli A, Sadelain M. Nat Med. 2018 June; 24(6):731-738.

Non-patent Document 9: New drugs, new toxicities: severe side effects of modern targeted and immunotherapy of cancer and their management. Kroschinsky F, Stolzel F, von Bonin S, Beutel G, Kochanek M, Kiehl M, Schellongowski P; Intensive Care in Hematological and Oncological Patients (iCHOP) Collaborative Group. Crit Care. 2017 Apr. 14; 21(1):89.

Non-patent Document 10: Toxicities of the anti-PD-1 and anti-PD-L1 immune checkpoint antibodies. J. Naidoo, D. B. Page, B. T. Li, L. C. Connell, K. Schindler, M. E. Lacouture, M. A. Postow & J. D. Wolchok. Annals of Oncology 26: 2375-2391, 2015

Non-patent Document 11: Immune-Related Adverse Events Associated with Anti-PD-1/PD-L1 Treatment for Malignancies: A Meta-Analysis. Wang P F, Chen Y, Song S Y, Wang T J, Ji W J, Li S W, Liu N, Yan C X. Front Pharmacol. 2017 Oct. 18; 8:730.

Non-patent Document 12: Tocilizumab for the management of immune mediated adverse events secondary to PD-1 blockade. Stroud C R, Hegde A, Cherry C, Naqash A R, Sharma N, Addepalli S, Cherukuri S, Parent T, Hardin J, Walker P. J Oncol Pharm Pract. 2017 Jan. 1:1078155217745144.

SUMMARY OF THE INVENTION

Problem to be Solved by the Invention

Under these circumstances, in CRS, irAEs, HLH, MAS and LCH, etc., there has been a demand for the development of a method for ameliorating these diseases or symptoms.

Means to Solve the Problem

As a result of extensive and intensive efforts made to solve the problems stated above, the inventors of the present invention have found that JTE-607 or a derivative thereof ameliorates the above diseases or symptoms. This finding led to the completion of the present invention.

Namely, the present invention is as follows.

(1) A medicament for at least one selected from the group consisting of cytokine release syndrome, autoimmune-related adverse events, macrophage activation syndrome, hemophagocytic lymphohistiocytosis and Langerhans cell histiocytosis, wherein the medicament comprises a compound represented by the following formula I:

[Formula 1]

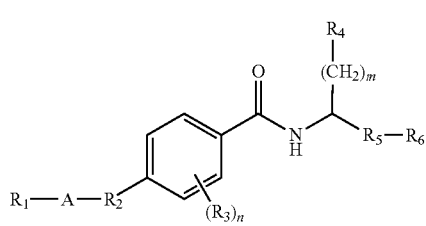

(I)

[wherein $R_1$ represents an optionally substituted nitrogen-containing non-aromatic alkyl group or an optionally substituted nitrogen-containing heterocyclyl group, A represents a single bond or an optionally substituted linear or branched alkylene group containing 1 to 10 carbon atoms which may have one or two or more double or triple bonds in the chain, $R_2$ represents an oxygen atom or a group represented by —CO—, —COO—, —OCO— or —O—CO—O—, each $R_3$, which may be the same or different, represents a hydrogen atom, a hydroxyl group, a halogen atom or an optionally substituted linear or branched alkyl group containing 1 to 20 carbon atoms (provided that at least one $R_3$ is not a hydrogen atom), n represents an integer of 1 to 4, m represents 0 or an integer of 1 to 6, $R_4$ represents an optionally substituted aryl group containing 6 to 20 carbon atoms, an optionally substituted heterocyclyl group, an optionally substituted cycloalkyl group containing 3 to 10 carbon atoms, an optionally substituted linear or branched alkyl group containing 1 to 20 carbon atoms, or an optionally substituted linear or branched alkoxy group containing 1 to 20 carbon atoms, $R_5$ represents an oxygen atom or a group represented by —CO—, —COO—, —OCO— or —O—CO—O—, and $R_6$ represents a hydrogen atom or a linear or branched alkyl group containing 1 to 20 carbon atoms or an optionally substituted aryl group containing 1 to 20 carbon atoms]
or a pharmaceutically acceptable salt thereof.

(2) The medicament according to (1) above, wherein the nitrogen-containing non-aromatic heterocyclyl group is a piperazinyl group or a piperidinyl group, A is a linear alkylene group containing 1 to 10 carbon atoms, $R_2$ is an oxygen atom, each $R_3$, which may be the same or different, is a hydrogen atom or a halogen atom (provided that at least one $R_3$ is not a hydrogen atom), $R_4$ is a phenyl group, $R_5$ represents a group represented by —COO—, and $R_6$ is a linear alkyl group containing 1 to 10 carbon atoms.

(3) The medicament according to (1) above, wherein the nitrogen-containing non-aromatic alkyl group is an alkylamino group, A is a linear alkylene group containing 1 to 10 carbon atoms, $R_2$ is an oxygen atom, each $R_3$, which may be the same or different, is a hydrogen atom or a halogen atom (provided that at least one $R_3$ is not a hydrogen atom), $R_4$ is a phenyl group, $R_5$ represents a group represented by —COO—, and $R_6$ is a linear alkyl group containing 1 to 10 carbon atoms.

(4) The medicament according to any one of (1) to (3) above, wherein the compound represented by formula I or a pharmaceutically acceptable salt thereof is a compound represented by the following formula II:

[Formula 2]

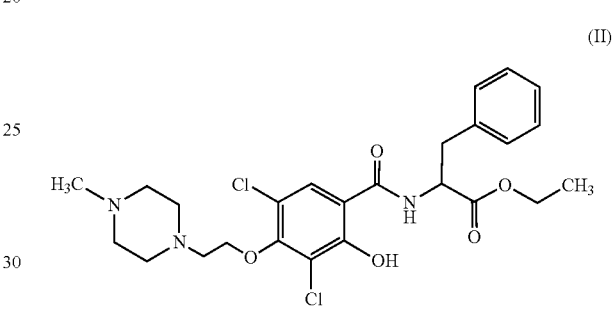

(II)

or a pharmaceutically acceptable salt thereof.

(5) The medicament according to any one of (1) to (4) above, wherein the compound represented by formula I or a pharmaceutically acceptable salt thereof is a compound represented by the following formula III:

[Formula 3]

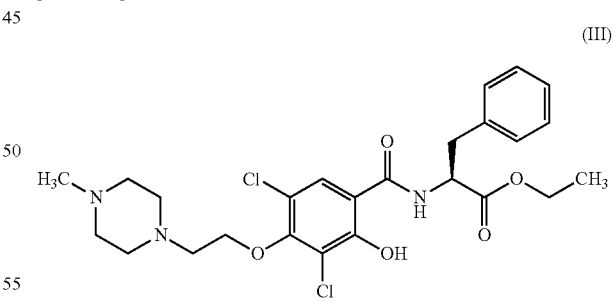

(III)

or a pharmaceutically acceptable salt thereof.

(6) The medicament according to any one of (1) to (5) above, wherein the compound represented by formula I or a pharmaceutically acceptable salt thereof is a hydrochloride salt of the compound represented by formula III.

(7) The medicament according to any one of (1) to (6) above, wherein the compound represented by formula I or a pharmaceutically acceptable salt thereof is a compound represented by the following formula IV:

[Formula 4]

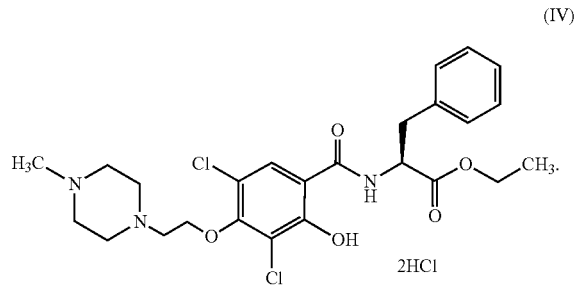

(IV)

[Formula 5]

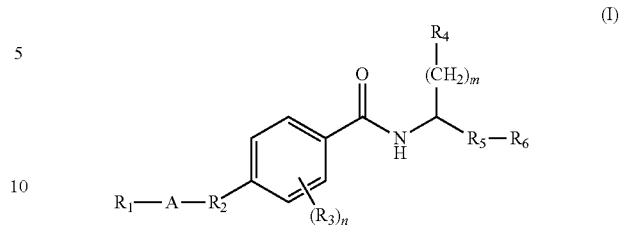

(I)

(8) The medicament according to any one of (1) to (7) above, wherein the diseases or symptoms are those due to the use of immune checkpoint inhibitors, those due to chimeric antigen receptor-expressing T cell therapy, those due to engineered T cell receptor-expressing T cell therapy, or those induced by at least one selected from the group consisting of infections, cancers and autoimmune diseases.

(9) The medicament according to any one of (1) to (8) above, which suppresses at least one of cytokine production and macrophage activation.

(10) The medicament according to any one of (1) to (9) above, wherein the cytokine is at least one selected from the group consisting of tumor necrosis factor (TNF)-α, interleukin (IL)-1β, IL-4, IL-6, IL-8, IL-1RA, IL-2Rα, IL-10, IL-18, granulocyte-macrophage colony-stimulating factor (GM-CSF), macrophage colony-stimulating factor (M-CSF), insulin growth factor (IGF), interferon (IFN)-γ, IFN-γ-induced protein 10 (IP-10), monocyte chemotactic protein (MCP)-1, vascular endothelial growth factor (VEGF), osteopontin (OPN), Receptor activator of NF-κB ligand (RANKL), cytokine receptor gp130, soluble IL-1 receptor (sIL-1R)-1, sIL-1R-2, soluble IL-6 receptor (sIL-6R), soluble receptor for advanced glycation end products (sRAGE), soluble TNF receptor (sTNFR)-1, sTNFR-2, monokine induced by IFN-γ (MIG), macrophage inflammatory protein (MIP)-1α and MIP-1β.

(11) The medicament according to (10) above, wherein the cytokine is at least one selected from the group consisting of TNF-α, IL-1β, IL-6, IL-8, IL-18, IFN-γ, MCP-1 and OPN.

(12) The medicament according to any one of (1) to (11) above for use in the prevention or amelioration of at least one selected from the group consisting of cytokine release syndrome, autoimmune-related adverse events, macrophage activation syndrome, hemophagocytic lymphohistiocytosis and Langerhans cell histiocytosis.

(13) The present invention further includes the following embodiments.

(13-1) A prophylactic, therapeutic or ameliorative agent for at least one selected from the group consisting of cytokine release syndrome, autoimmune-related adverse events, macrophage activation syndrome, hemophagocytic lymphohistiocytosis and Langerhans cell histiocytosis, wherein the agent comprises a compound represented by the following formula I:

[wherein $R_1$ represents an optionally substituted nitrogen-containing non-aromatic alkyl group or an optionally substituted nitrogen-containing heterocyclyl group, A represents a single bond or an optionally substituted linear or branched alkylene group containing 1 to 10 carbon atoms which may have one or two or more double or triple bonds in the chain, $R_2$ represents an oxygen atom or a group represented by —CO—, —COO—, —OCO— or —O—CO—O—, each $R_3$, which may be the same or different, represents a hydrogen atom, a hydroxyl group, a halogen atom or an optionally substituted linear or branched alkyl group containing 1 to 20 carbon atoms (provided that at least one $R_3$ is not a hydrogen atom), n represents an integer of 1 to 4, m represents 0 or an integer of 1 to 6, $R_4$ represents an optionally substituted aryl group containing 6 to 20 carbon atoms, an optionally substituted heterocyclyl group, an optionally substituted cycloalkyl group containing 3 to 10 carbon atoms, an optionally substituted linear or branched alkyl group containing 1 to 20 carbon atoms, or an optionally substituted linear or branched alkoxy group containing 1 to 20 carbon atoms, $R_5$ represents an oxygen atom or a group represented by —CO—, —COO—, —OCO— or —O—CO—O—, and $R_6$ represents a hydrogen atom or a linear or branched alkyl group containing 1 to 20 carbon atoms or an optionally substituted aryl group containing 1 to 20 carbon atoms]
or a pharmaceutically acceptable salt thereof.

(13-2) A prophylactic, therapeutic or ameliorative method for at least one selected from the group consisting of cytokine release syndrome, autoimmune-related adverse events, macrophage activation syndrome, hemophagocytic lymphohistiocytosis and Langerhans cell histiocytosis, wherein the method comprises administering a compound represented by formula I appearing above (wherein $R_1$, $R_2$, $R_3$, $R_4$, $R_5$, $R_6$, m and n are as defined above) or a pharmaceutically acceptable salt thereof to a mammal.

(13-3) The use of a compound represented by formula I appearing above (wherein $R_1$, $R_2$, $R_3$, $R_4$, $R_5$, $R_6$, m and n are as defined above) or a pharmaceutically acceptable salt thereof for the manufacture of a medicament for use in the prevention, treatment or amelioration of at least one selected from the group consisting of cytokine release syndrome, autoimmune-related adverse events, macrophage activation syndrome, hemophagocytic lymphohistiocytosis and Langerhans cell histiocytosis.

(13-4) A compound represented by formula I appearing above (wherein $R_1$, $R_2$, $R_3$, $R_4$, $R_5$, $R_6$, m and n are as defined above) or a pharmaceutically acceptable salt thereof for use in the prevention, treatment or amelioration of at least one selected from the group consisting of cytokine release syndrome, autoimmune-related adverse events, macrophage activation syndrome, hemophagocytic lymphohistiocytosis and Langerhans cell histiocytosis.

(14) In one embodiment of formula I appearing in (13) above, the nitrogen-containing non-aromatic heterocyclyl group is a piperazinyl group or a piperidinyl group, A is a linear alkylene group containing 1 to 10 carbon atoms, $R_2$ is an oxygen atom, each $R_3$, which may be the same or different, is a hydrogen atom or a halogen atom (provided that at least one $R_3$ is not a hydrogen atom), $R_4$ is a phenyl group, $R_5$ represents a group represented by —COO—, and $R_6$ is a linear alkyl group containing 1 to 10 carbon atoms.

In another embodiment, the nitrogen-containing non-aromatic alkyl group is an alkylamino group, A is a linear alkylene group containing 1 to 10 carbon atoms, $R_2$ is an oxygen atom, each $R_3$, which may be the same or different, is a hydrogen atom or a halogen atom (provided that at least one $R_3$ is not a hydrogen atom), $R_4$ is a phenyl group, $R_5$ represents a group represented by —COO—, and $R_6$ is a linear alkyl group containing 1 to 10 carbon atoms.

In another embodiment of formula I appearing in (13) above, the compound represented by formula I or a pharmaceutically acceptable salt thereof is a compound represented by the following formula II:

[Formula 6]

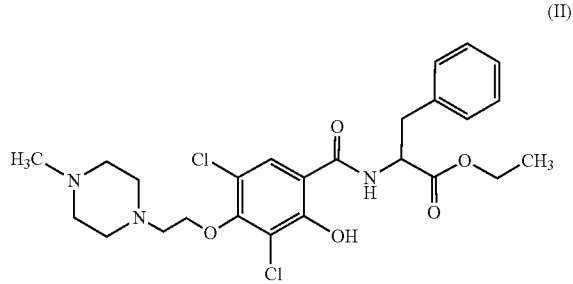 [SMILES: CCOC(=O)C(Cc1ccccc1)NC(=O)c1cc(Cl)c(OCCN2CCN(C)CC2)c(Cl)c1O]

(II)

or a pharmaceutically acceptable salt thereof, preferably a compound represented by the following formula III:

[Formula 7]

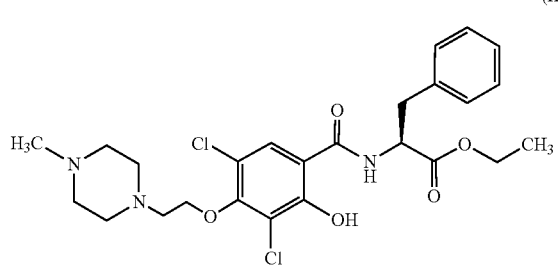

(III)

or a pharmaceutically acceptable salt thereof. In a more preferred embodiment, the compound represented by formula I or a pharmaceutically acceptable salt thereof is a hydrochloride salt of the compound represented by formula III.

In yet another embodiment of formula I appearing in (13) above, the compound represented by formula I or a pharmaceutically acceptable salt thereof is a compound represented by the following formula IV:

[Formula 8]

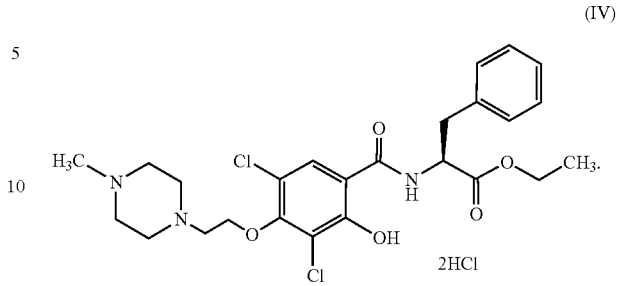

(IV)

(15) In (13) above, the diseases or symptoms are those due to the use of immune checkpoint inhibitors, those due to chimeric antigen receptor-expressing T cell therapy, those due to engineered T cell receptor-expressing T cell therapy, or those induced by at least one selected from the group consisting of infections, cancers and autoimmune diseases, and the compounds represented by formulae I to IV or pharmaceutically acceptable salts thereof suppress at least one of cytokine production and macrophage activation. The cytokine intended here is exemplified by at least one selected from the group consisting of TNF-α, IL-1β, IL-4, IL-6, IL-8, IL-1RA, IL-2Rα, IL-10, IL-18, GM-CSF, M-CSF, IGF, IFN-γ, IP-10, MCP-1, VEGF, OPN, RANKL, cytokine receptor gp130, sIL-1R-1, sIL-1R-2, sIL-6R, sRAGE, sTNFR-1, sTNFR-2, MIG, MIP-1α and MIP-1β, and preferred is at least one selected from the group consisting of TNF-α, IL-1β, IL-6, IL-8, IL-18, IFN-γ, MCP-1 and OPN.

Effects of the Invention

The present invention provides a medicament for at least one selected from the group consisting of CRS, irAEs, HLH, MAS and LCH. The medicament comprising a compound represented by formula I or a pharmaceutically acceptable salt thereof has the potential to suppress the release of inflammatory cytokines to thereby ameliorate or prevent these symptoms and, in turn, to relatively enhance the effects of CAR-T cell therapy and immune checkpoint inhibitors.

DESCRIPTION OF EMBODIMENTS

The present invention will be described in more detail below.

1. Summary

The present invention is directed to a medicament for at least one selected from the group consisting of cytokine release syndrome (CRS), autoimmune-related adverse events (irAEs), macrophage activation syndrome (MAS), hemophagocytic lymphohistiocytosis (HLH) and Langerhans cell histiocytosis (LCH), wherein the medicament comprises a compound represented by the following formula I:

[Formula 9]

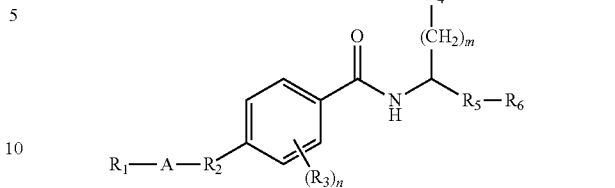

or a pharmaceutically acceptable salt thereof, and this medicament can be used as a prophylactic or ameliorative agent for these diseases or symptoms and also can be used in the form of a pharmaceutical composition comprising various additives.

In a compound represented by formula I or a pharmaceutically acceptable salt thereof (also collectively referred to as "the compound of the present invention"), the inventors of the present invention have now constructed an evaluation system capable of reproducing CRS toxicity through target cell recognition by CD19-CAR-T cells and CD8+ T cell activation induced by magnetic beads covalently attached with anti-CD3 and anti-CD28 antibodies (i.e., T-cell stimulation beads) to investigate the effect of this compound (e.g., JTE-607) in comparison with the effect of an existing drug, PSL. The results have indicated that PSL predominantly suppresses T cell functions (immunosuppression: suppression of CAR-T cell functions and CD8+ functions) but shows a weak suppressive effect on the production of IL-6 and other inflammatory cytokines, whereas JTE-607 is characterized by strongly suppressing the production of IL-6 and other inflammatory cytokines in a dose-dependent manner, and its effects on CAR-T cells, CD4− functions and CD8− functions (e.g., cytotoxicity against target cancer cells, IFN-γ production ability) are limited and not dose-dependent. Moreover, it has been indicated that JTE-607 suppresses not only IL-6 production but also IL-18 and Osteopontin (OPN) production in a dose-dependent manner, whereas tocilizumab has no suppressive effect on the production of these cytokines.

Figure 26:
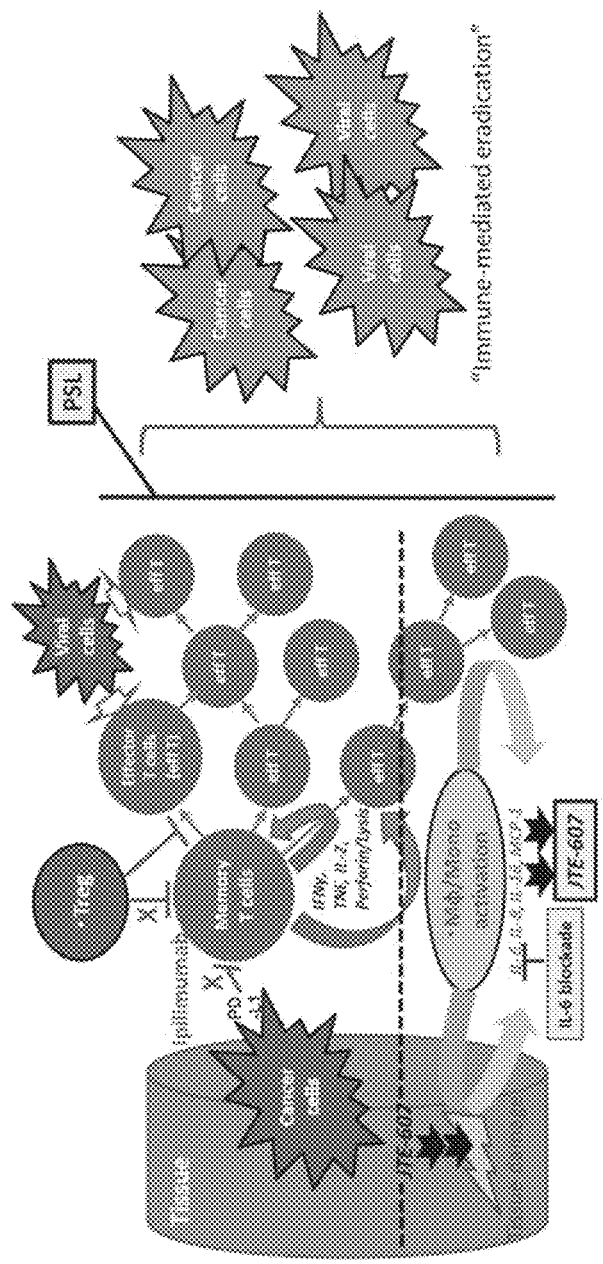
FIG. 26 summarizes the mechanism of action for the compound of the present invention.

FIG. 26 shows the mechanism of action for the compound of the present invention. In FIG. 26, the excessive reaction of endogenous T effector cells induces a series of diseases or symptoms along with monocyte/macrophage activation (FIG. 26, the area below the broken line). The compound of the present invention can be used for prevention or amelioration (including treatment) of these diseases or symptoms. In view of the foregoing, the compound of the present invention as a medicament for at least one disease or symptom selected from the group consisting of CRS, irAEs, HLH, MAS and LCH may serve, for example, as a therapeutic tool effective in the amelioration and/or prevention of CRS toxicity concurrently occurring in CAR-T cell therapy. Thus, the present invention provides a prophylactic method or an ameliorative or therapeutic method for at least one disease or symptom selected from the group consisting of CRS, irAEs, HLH, MAS and LCH, wherein the method comprises the step of administering the compound of the present invention or a medicament comprising the compound of the present invention to a patient with the disease or symptom.

Moreover, also in the case of hypercytokinemia-like symptoms concurrently occurring upon administration of immune checkpoint inhibitors such as bi-specific antibody and PD1/CTLA4 antibody which serve as enhancers for potential T cell functions, these CRS-like symptoms irAEs can be ameliorated without significantly affecting the enhanced T cell functions.

As used herein, the term "prevention" or "prophylactic" is intended to mean that the above diseases or symptoms are prevented from developing in a patient who may be predisposed to the above diseases or symptoms but has not yet been diagnosed as having them.

The term "treatment" or "therapeutic" is intended to mean that the above diseases or symptoms are inhibited, i.e., their progression is arrested or delayed or disappears.

The term "amelioration" or "ameliorative" is intended to mean that the above diseases or symptoms are alleviated, i.e., the recession of the above diseases or symptoms is caused or the progression of the symptoms is reversed.

2. Compounds or Pharmaceutically Acceptable Salts Thereof

In the present invention, a compound serving as an active ingredient, which is used as a medicament for at least one disease or symptom selected from the group consisting of CRS, irAEs, HLH, MAS and LCH (e.g., a prophylactic, therapeutic or ameliorative agent for these diseases), is represented by the following formula I. Among compounds falling within the present invention, a compound represented by formula I is also referred to as "compound (I)."

[Formula 10]

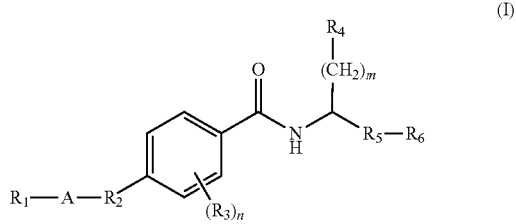

(I)

In the formula, $R_1$ represents a nitrogen-containing non-aromatic alkyl group or an optionally substituted nitrogen-containing heterocyclyl group.

A represents a single bond or an optionally substituted linear or branched alkylene group containing 1 to 20 carbon atoms which may have one or two or more double or triple bonds in the chain. A is preferably a linear alkylene group containing 1 to 6 carbon atoms, and more preferably an ethylene group.

$R_2$ represents an oxygen atom or a group represented by —CO—, —COO—, —OCO— or —O—CO—O—.

Each $R_3$, which may be the same or different, represents a hydrogen atom, a hydroxyl group, a halogen atom or an optionally substituted linear or branched alkyl group containing 1 to 20 carbon atoms, provided that at least one $R_3$ is not a hydrogen atom.

n represents an integer of 1 to 4, and is preferably 3, two of which are halogen atoms, and the other one is a hydroxyl group in a more preferred embodiment.

$R_4$ represents an optionally substituted aryl group containing 6 to 20 carbon atoms, an optionally substituted heterocyclyl group, an optionally substituted cycloalkyl group containing 3 to 10 carbon atoms, an optionally substituted linear or branched alkyl group containing 1 to 20 carbon atoms, or an optionally substituted linear or branched alkoxy group containing 1 to 20 carbon atoms. m represents 0 or an integer of 1 to 6, and is preferably 2.

$R_5$ represents an oxygen atom or a group represented by —CO—, —COO—, —OCO— or —O—CO—O—, and is preferably a group represented by —COO—.

$R_6$ represents a hydrogen atom or a linear or branched alkyl group containing 1 to 20 carbon atoms or an optionally substituted aryl group containing 6 to 20 carbon atoms, but it is preferably a linear alkyl group containing 1 to 6 carbon atoms, and more preferably an ethyl group.

The term "nitrogen-containing non-aromatic alkyl group" refers to an alkyl group containing 1 to 10 carbon atoms which has at least one nitrogen atom, as exemplified by a methylamino group.

The term "nitrogen-containing non-aromatic heterocyclyl group" is intended to mean a 3- to 7-membered non-aromatic heterocyclyl group which has at least one nitrogen atom and which may have a sulfur atom or an oxygen atom, and this group may be fused with a benzene ring. Specific examples include an aziridinyl group, a thiazetidinyl group, an azetidinyl group, a pyrrolidinyl group, a pyrrolinyl group, an imidazolidinyl group, an imidazolinyl group, a pyrazolidinyl group, a pyrazolinyl group, a morpholinyl group, a morpholino group, an oxazinyl group, a thiazinyl group, a piperazinyl group, a piperidyl group, a piperidino group, a dioxazepinyl group, a thiazepinyl group, a diazepinyl group, a perhydrodiazepinyl group, an azepinyl group, a perhydroazepinyl group, an indolinyl group, an isoindolinyl group and so on. Preferred are an aziridinyl group, an azetidinyl group, a pyrrolidinyl group, a pyrazolidinyl group, a morpholinyl group, a morpholino group, a piperazinyl group, a piperidyl group, a piperidino group and a perhydroazepinyl group, and particularly preferred are a piperazinyl group and a piperidyl group.

The term "alkylene group" is intended to mean a linear or branched alkylene group which may have one or two or more double or triple bonds in the linear or branched chain. Examples of a linear or branched alkylene group containing 1 to 20 carbon atoms include a methylene group, an ethylene group, a trimethylene group, a tetramethylene group, a pentamethylene group, a hexamethylene group, a heptamethylene group, an octamethylene group, a nonamethylene group, a decamethylene group, a dimethylmethylene group, a diethylmethylene group, a propylene group, a methylethylene group, an ethylethylene group, a propylethylene group, an isopropylethylene group, a methylpentamethylene group, an ethylhexamethylene group, a dimethylethylene group, a methyltrimethylene group, a dimethyltrimethylene group, a vinylene group, a propenylene group, a butenylene group, a butadienylene group, a pentenylene group, a pentadienylene group, a hexenylene group, a hexadienylene group, a hexatrienylene group, a heptenylene group, a heptadienylene group, a heptatrienylene group, an octenylene group, an octadienylene group, an octatrienylene group, an octatetraenylene group, a propynylene group, a butynylene group, a pentynylene group, a methylpropynylene group and so on.

Preferred are linear alkylene groups, such as a methylene group, an ethylene group, a trimethylene group, a tetramethylene group, a pentamethylene group, a hexamethylene group, a heptamethylene group, an octamethylene group, a nonamethylene group, a decamethylene group, a vinylene group, a propenylene group, a butenylene group, a butadienylene group, a pentenylene group, a pentadienylene group, a hexenylene group, a hexadienylene group, a hexatrienylene group, a heptenylene group, a heptadienylene group, a heptatrienylene group, an octenylene group, an octadienylene group, an octatrienylene group, an octatetraenylene group, a propynylene group, a butynylene group, a pentynylene group, etc. More preferred are linear alkylene groups containing 1 to 6 carbon atoms, such as a methylene group, an ethylene group, a trimethylene group, a tetramethylene group, a pentamethylene group, a hexamethylene group, etc.

The term "alkyl group" refers to an alkyl group which is linear, branched, or a combination thereof, and contains 1 to 20 carbon atoms, preferably 1 to 10 carbon atoms or 1 to 6 carbon atoms.

The above alkyl group may be exemplified by a methyl group, an ethyl group, a n-propyl group, an isopropyl group, a n-butyl group, an isobutyl group, a s-butyl group, a tert-butyl group, a n-pentyl group, an isopentyl group, a 2-methylbutyl group, a neopentyl group, a 1-ethylpropyl group, a n-hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, n-eicosyl group and so on. The alkoxy group intended herein is an alkoxy group containing 1 to 20 carbon atoms whose alkyl moiety is the same as the alkyl group described above.

Examples of an aryl group containing 6 to 20 carbon atoms include a phenyl group, a 1-naphthyl group, a 2-naphthyl group, an indenyl group, a biphenyl group, an anthryl group, a phenanthryl group and so on.

A heterocyclyl group refers to a 3- to 7-membered non-aromatic heterocyclyl group which may have at least one nitrogen atom, sulfur atom or oxygen atom, and its actual substituents are the same as described above for the "nitrogen-containing non-aromatic heterocyclyl group."

Examples of a cycloalkyl group containing 3 to 10 carbon atoms include a cyclopropyl group, a cyclobutyl group, a cyclopentyl group, a cyclohexyl group, a cycloheptyl group, a cyclooctyl group and so on.

When the expression "may have a substituent(s)" or "optionally substituted" is used herein to describe a certain functional group, it means that this functional group may have one or two or more "substituents" at a chemically possible position(s), unless otherwise specified. The type, number and position of substituents present on a functional group are not limited in any way, and when two or more substituents are present, they may be the same or different. Examples of a "substituent" present on a functional group include, but are not limited to, an alkyl group, an alkenyl group, an alkynyl group, an alkoxy group, an aryl group, a halogen atom, an oxo group, a thioxo group, a nitro group, a nitroso group, a cyano group, an isocyano group, a cyanato group, a thiocyanato group, an isocyanato group, an isothiocyanato group, a hydroxy group, a sulfanyl group, a carboxy group, a sulfanylcarbonyl group, an oxalo group, a mesoxalo group, a thiocarboxy group, a dithiocarboxy group, a carbamoyl group, a thiocarbamoyl group, a sulfo group, a sulfamoyl group, a sulfino group, a sulfinamoyl group, a sulfeno group, a sulfenamoyl group, a phosphono group, a hydroxyphosphonyl group, a heterocyclyl group, a heterocyclyl-oxy group, an alkylsulfanyl group, an acyl group, an amino group, a hydrazino group, a hydrazono group, a diazenyl group, a ureido group, a thioureido group, a guanidino group, an amidino group, an azido group, an imino group, a hydroxyamino group, a hydroxyimino group, an aminooxy group, a diazo group, a semicarbazino group, a semicarbazono group, an allophanyl group, a hydantoyl group, a phosphano group, a phosphoroso group, a phospho group, a boryl group, a silyl group, a stannyl group, a selanyl group, an oxide group and so on.

A salt of compound (I) may be exemplified by salts with inorganic acids or organic acids (i.e., acid addition salts). Examples of such an inorganic acid include hydrochloric acid, sulfuric acid, phosphoric acid, hydrobromic acid, nitric acid and so on, while examples of such an organic acid include oxalic acid, maleic acid, fumaric acid, malic acid, tartaric acid, succinic acid, citric acid, acetic acid, lactic acid, methanesulfonic acid, paratoluenesulfonic acid, benzoic acid, valeric acid, malonic acid, nicotinic acid, propionic acid and so on.

A preferred acid addition salt in the present invention is a salt with hydrochloric acid, more preferably a dihydrochloride salt.

Compound (I) may have one or two or more stereoisomers based on its asymmetric carbon. The present invention also encompasses these isomers and a mixture thereof. Further, compound (I) or a pharmaceutically acceptable salt thereof may be in the form of a hydrate, a solvate with a pharmacologically acceptable organic solvent (e.g., ethanol) or a prodrug, each of which also falls within the present invention.

The term "prodrug" refers to a derivative of the compound of the present invention, which has a chemically or metabolically degradable group, so that after being administered in vivo, it is restored to the original compound to exert its inherent efficacy. Such a prodrug includes a non-covalently bonded complex and a salt.

A prodrug of compound (I) may be exemplified by compounds designed such that the carboxyl group in compound (I) is modified with an ethyl group, a pivaloyloxymethyl group, a 1-(acetyloxy)ethyl group, a 1-(ethoxycarbonyloxy)ethyl group, a 1-(cyclohexyloxycarbonyloxy)ethyl group, a carboxylmethyl group, a (5-methyl-2-oxo-1,3-dioxol-4-yl)methyl group, a phenyl group, an o-tolyl group, etc. Other examples include compounds designed such that the hydroxyl group in compound (I) is modified with an acetyl group, a propionyl group, an isobutyryl group, a pivaloyl group, a benzoyl group, a 4-methylbenzoyl group, a dimethylcarbamoyl group, a sulfo group, etc.

In the present invention, compound (I) is preferably exemplified by (−)-ethyl N-{3,5-dichloro-2-hydroxy-4-[2-(4-methylpiperazin-1-yl)ethoxy]benzoyl}-L-phenylalaninate represented by the following formula III:

[Formula 11]

(III)

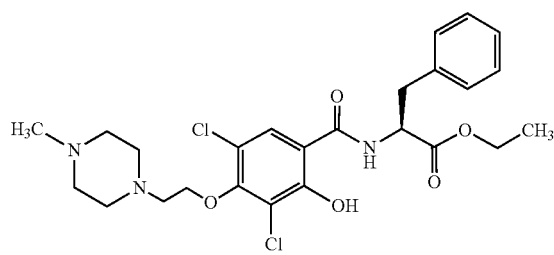

(i.e., N-{3,5-dichloro-2-hydroxy-4-[2-(4-methylpiperazin-1-yl)ethoxy]benzoyl}-L-phenylalanine ethyl ester) or a pharmacologically acceptable salt thereof.

The compound to be used in the present invention is more preferably an acid addition salt (e.g., a dihydrochloride salt) of the above compound represented by formula II(III?), and even more preferably a compound represented by formula IV:

[Formula 12]

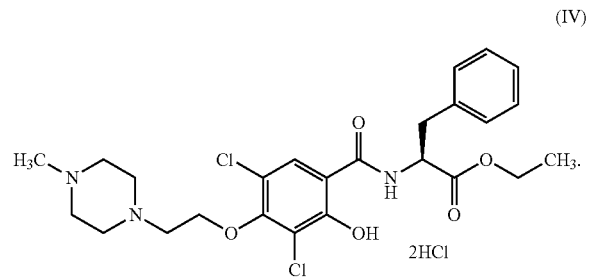

(IV)

The compound represented by formula IV is (−)-ethyl N-{3,5-dichloro-2-hydroxy-4-[2-(4-methylpiperazin-1-yl)ethoxy]benzoyl}-L-phenylalaninate dihydrochloride (i.e., N-{3,5-dichloro-2-hydroxy-4-[2-(4-methylpiperazin-1-yl)ethoxy]benzoyl}-L-phenylalanine ethyl ester dihydrochloride), which is also known as "JTE-607."

The compound of the present invention suppresses the production of various inflammatory cytokines which are produced in animals (e.g., mammals such as rats, mice, rabbits, pigs, cats, dogs, cows, horses, monkeys, humans, etc.).

In the present invention, it is particularly effective as a medicament for one or more diseases or symptoms of CRS, irAEs, HLH, MAS and LCH.

For example, in human cytokine release syndrome, the compound of the present invention is particularly effective against CRS and cerebral edema in CAR-T cell therapy. Thus, the compound of the present invention can be used in combination with CAR-T cell therapy. The expression "used in combination" is intended to mean that the compound of the present invention is used concurrently with CAR-T cell therapy, but the timing for use in combination is not limited in any way and may be any timing of before CAR-T cell therapy, during CAR-T cell therapy and after CAR-T cell therapy. With regard to irAEs, HLH, MAS and LCH, the compound of the present invention can also be used concurrently with drugs or therapies used in the treatment of these diseases or symptoms, as in the case of CRS.

The compound of the present invention allows suppression of cytokine production, suppression of macrophage activation, or suppression of both cytokine production and macrophage activation. As used herein, the term "macrophage activation" is intended to mean the excessive release of various cytokines, cytotoxic proteases and/or active oxygen species, etc., as well as the enhancement of opsonization and/or phagocytic activity, etc.

The term "cytokine" is intended to include, for example, tumor necrosis factor (TNF)-α, IL-1β, IL-4, IL-6, IL-8, IL-1RA, IL-2Rα, IL-10, IL-18, granulocyte-macrophage colony-stimulating factor (GM-CSF), macrophage colony-stimulating factor (M-CSF), insulin growth factor (IGF), interferon (IFN)-γ, IFN-γ-induced protein 10 (IP-10), monocyte chemotactic protein (MCP)-1, vascular endothelial growth factor (VEGF), osteopontin (OPN), Receptor activator of NF-κB ligand (RANKL), cytokine receptor gp130, soluble IL-1 receptor (sIL-1R)-1, sIL-1R-2, soluble IL-6 receptor (sIL-6R), soluble receptor for advanced glycation end products (sRAGE), soluble TNF receptor (sTNFR)-1, sTNFR-2, monokine induced by IFN-γ (MIG), macrophage inflammatory protein (MIP)-1α, MIP-1β and so on.

irAEs refer primarily to a group of adverse events associated with immune checkpoint inhibitors whose administration results in excessive activation of overall immunity and thereby induces self-attack to cause various symptoms of autoimmune diseases. Major symptoms include interstitial lung disease, colitis, hypothyroidism, hepatopathy, exanthema, hypophysitis, diabetes, renal dysfunction, peripheral neuropathy, myasthenia gravis and so on, which have been reported in all organs throughout the body.

HLH refers to a disease caused by defects in genes which are involved in cytotoxic granules and their release. This disease is characterized by pathologies such as tissue damage and macrophage expansion associated with hypercytokinemia. As to inflammatory cytokines involved in HLH, there have been reported IFN-γ, IL-1β, IL-6, IL-18, TNF-α and so on.

MAS refers to a lethal pathological condition where inflammatory cytokines are in excessive levels, which is induced upon abnormal activation of macrophages in response to exogenous factors (e.g., viruses, bacteria, fungi and other infectious factors or drugs) or endogenous factors (e.g., debris generated upon apoptosis/necrosis of autologous cells), for example, proliferation and activation of virus-reactive T cell effectors. As to inflammatory cytokines involved in MAS, there have been reported IFN-γ, IL-1β, IL-6, IL-18, TNF-α and soon. HLH and MAS are similar to each other, but HLH is confirmed by pathological diagnosis, whereas MAS is confirmed by physiological diagnosis. In either pathological condition, macrophage activation plays an important role.

LCH[13] refers to a pathological condition showing abnormal expansion of Langerhans cells in the skin, bone, lymph nodes and other organs. In lesion sites, there are observed not only Langerhans cells, but also inflammatory infiltrates including eosinophils, lymphocytes, macrophages, osteoclast-like giant cells, etc., and these cells have been known to activate each other to thereby cause oversecretion of inflammatory cytokines/chemokines, as typified by OPN, RANKL, IL-18, C—C motif chemokine 2 (CCL2), etc., which in turn causes tissue destruction.

These diseases or symptoms are due to the use of immune checkpoint inhibitors, chimeric antigen receptor-expressing T cell therapy, engineered T cell receptor-expressing T cell therapy, etc., or are induced by any of infections, cancers and autoimmune diseases or any combination thereof.

An immune checkpoint inhibitor refers to a drug which binds to an immune checkpoint molecule (a group of molecules which suppress autoimmune responses and also suppress excessive immune reactions) or a ligand thereof to thereby inhibit immunosuppressive signaling and thus cancel the immune checkpoint molecule-suppressed activation of T cells. Examples include anti-CTLA-4 antibody, anti-PD-1 antibody, anti-PD-L1 antibody and so on.

CAR-T cell therapy is an autologous T cell therapy designed such that T cells taken from a patient are genetically engineered to express a targetable chimeric antigen receptor (CAR) and then returned into the patient's body.

Engineered T cell receptor-expressing T (TCAR-T) cell therapy is a therapy designed such that a particular TCR gene which recognizes a cancer antigen epitope in a particular human leukocyte antigen (HLA)-restricted manner is introduced into and amplified in effector T cells in vitro and then administered in vivo, by way of example. This cell therapy is similar to CAR-T cell therapy.

Preferred embodiments of the medicament according to (1) above are as listed below.

A medicament for at least one selected from the group consisting of cytokine release syndrome, macrophage activation syndrome and hemophagocytic lymphohistiocytosis, each being due to chimeric antigen receptor-expressing T cell therapy.

A medicament for cytokine release syndrome due to chimeric antigen receptor-expressing T cell therapy.

A medicament for macrophage activation syndrome due to chimeric antigen receptor-expressing T cell therapy.

A medicament for hemophagocytic lymphohistiocytosis due to chimeric antigen receptor-expressing T cell therapy.

A medicament for at least one selected from the group consisting of cytokine release syndrome, macrophage activation syndrome and hemophagocytic lymphohistiocytosis for use in combination with chimeric antigen receptor-expressing T cell therapy, wherein the medicament comprises a compound represented by formula I or a pharmaceutically acceptable salt thereof.

A medicament for at least one selected from the group consisting of cytokine release syndrome, macrophage activation syndrome and hemophagocytic lymphohistiocytosis, each being due to engineered T cell receptor-expressing T cell therapy.

A medicament for cytokine release syndrome due to engineered T cell receptor-expressing T cell therapy.

A medicament for macrophage activation syndrome due to engineered T cell receptor-expressing T cell therapy.

A medicament for hemophagocytic lymphohistiocytosis due to engineered T cell receptor-expressing T cell therapy.

A medicament for at least one selected from the group consisting of cytokine release syndrome, macrophage activation syndrome and hemophagocytic lymphohistiocytosis for use in combination with engineered T cell receptor-expressing T cell therapy, wherein the medicament comprises a compound represented by formula I or a pharmaceutically acceptable salt thereof.

For use as a "medicament for cytokine release syndrome due to chimeric antigen receptor-expressing T cell therapy" and as a "medicament for cytokine release syndrome due to engineered T cell receptor-expressing T cell therapy," preferred are medicaments suppressing the production of at least one, more preferably a plurality of cytokines selected from the group consisting of TNF-α, IL-1β, IL-6, IL-8, IFN-γ and MCP-1.

A medicament for macrophage activation syndrome.

Preferred for this purpose is a medicament suppressing the production of at least one, more preferably a plurality of cytokines selected from the group consisting of TNF-α, IL-1β, IL-6, IL-18, IFN-γ and MCP-1.

A medicament for hemophagocytic lymphohistiocytosis.

Preferred for this purpose is a medicament suppressing the production of at least one, more preferably a plurality of cytokines selected from the group consisting of TNF-α, IL-1β, IL-6, IL-8, IL-18, IFN-γ and MCP-1.

A medicament for autoimmune-related adverse events due to the use of immune checkpoint inhibitors. Preferred for this purpose is a medicament suppressing the production of at least one, more preferably a plurality of cytokines selected from the group consisting of TNF-α, IL-1β, IL-6, IL-18 and IFN-γ.

A medicament for Langerhans cell histiocytosis induced by autoimmune diseases. Preferred for this purpose is a medicament suppressing the production of at least one, more preferably a plurality of cytokines selected from the group consisting of IL-18, MCP-1 and OPN.

Moreover, for use as a "medicament for at least one selected from the group consisting of cytokine release syndrome, autoimmune-related adverse events, macrophage activation syndrome, hemophagocytic lymphohistiocytosis and Langerhans cell histiocytosis, wherein the medicament comprises a compound represented by formula I or a pharmaceutically acceptable salt thereof," preferred is a medicament suppressing the production of at least one, more preferably a plurality of cytokines selected from the group consisting of IL-18, MCP-1 and OPN.

The compound of the present invention may be administered directly as a medicament (e.g., a prophylactic, therapeutic or ameliorative agent) for at least one selected from the group consisting of CRS, irAEs, HLH, MAS and LCH, although it is administered in the form of a pharmaceutical composition in one embodiment of the present invention. For use as a pharmaceutical composition containing the compound of the present invention as an active ingredient, this pharmaceutical composition may usually be formulated in any dosage form such as tablets, pills, powders, granules, suppositories, injections, eye drops, solutions, capsules, troches, aerosols, elixirs, suspensions, emulsions, syrups and so on in admixture with pharmacologically acceptable additives, as exemplified by pharmacologically acceptable carriers, excipients, diluents, extenders, disintegrants, stabilizers, preservatives, buffers, emulsifiers, flavorings, colorants, sweeteners, thickeners, correctives, solubilizers and/or other additives (e.g., water, vegetable oils, alcohols (e.g., ethanol or benzyl alcohol), polyethylene glycol, glycerol triacetate, gelatin, lactose, carbohydrates, magnesium stearate, talc, lanolin, white petrolatum, etc.).

For oral administration, the pharmaceutical composition may comprise a diluent, a dispersant and/or a surfactant in the form of powder or granules. For example, it may be present in water, in a syrup, in a dry state in a capsule or sachet, in a non-aqueous solution or suspension which may contain a suspending agent, or in a tablet which may contain a binder and a lubricant. The pharmaceutical composition may also comprise a sweetener, a corrective, a preservative (e.g., an antimicrobial preservative), a suspending agent, a thickener and/or an emulsifier.

For parenteral administration, the pharmaceutical composition is in the dosage form of a solution or suspension and may contain the compound of the present invention (e.g., compound (III)) and purified water. Additional ingredients which may be contained in a solution or suspension include a preservative (e.g., an antimicrobial preservative), a buffer, a solution thereof and a mixture thereof. The ingredients of the pharmaceutical composition may exert one or more functions. The pharmaceutical composition may be filled into single-dose or multiple-dose containers, e.g., sealed vials and ampules for storage in a lyophilized state, and may be added to a sterile liquid carrier (e.g., water or physiological saline) before use. In a preferred embodiment, the compound of the present invention (e.g., compound (III) or a pharmaceutically acceptable salt thereof) is formulated into a lyophilized formulation containing the same together with D-mannitol. Such a lyophilized formulation is preferably diluted with physiological saline before use.

Such a pharmaceutical composition containing the compound of the present invention may be prepared in a manner well known in the field of medicaments, for example, by the method described in Gennaro, et al., "Remington's Pharmaceutical Sciences" 18th ed., Mack Publishing CO., 1990, particularly Part 8: "Pharmaceutical Preparation and their Manufacture." This method comprises the step of associating the compound of the present invention with the other ingredients of the pharmaceutical composition.

The medicament of the present invention may be administered in an appropriate manner, and the route of its administration is not limited in any way. Examples include oral, buccal, nasal, percutaneous, injection, sustained release, controlled release, iontophoresis and sonophoresis. The route of injection is not limited in any way but includes parenteral routes such as intravenous, intramuscular, subcutaneous, intraperitoneal, intraspinal, intrathecal, intracerebroventricular, intraarterial and other routes of injection. For parenteral administration, the pharmaceutical composition may be formulated as a liquid or non-liquid sterile injection formulation, with an intravenous injection formulation being preferred.

The suitable dose of the compound of the present invention will vary depending on the patient's type and symptoms, the route of administration, sexual difference, body weight, etc. For oral administration in adults, for example, the daily dose of the compound of the present invention (particularly compound (III) or a pharmaceutically acceptable salt thereof) is usually about 0.01 to 1,000 mg (e.g., 0.05 to 900 mg, preferably 0.1 to 100 mg).

For intravenous administration in adults, for example, the daily dose of the compound of the present invention (particularly compound (III) or a pharmaceutically acceptable salt thereof) is usually about 0.01 to 100 mg/kg (e.g., about 0.01 to 95 mg/kg, preferably about 0.01 to 50 mg/kg), which may be given as a single dose or in divided doses (e.g., 2, 3, 4, 5, 6, 7, 8, 9, 10 or more doses). Alternatively, the compound of the present invention (particularly compound (III) or a pharmaceutically acceptable salt thereof) may be administered by continuous intravenous administration over the selected period of time (e.g., several hours to one or more days). The total daily dose for continuous administration is usually the same as the daily dose used in non-continuous intravenous administration.

EXAMPLES

The present invention will be further described in more detail below by way of the following illustrative examples. However, the scope of the present invention is not limited to these examples.

Example 1

1. Method
1.1 Materials
1.1.1 Cells
   Cryopreserved Human PBMCs (PBMCs): BIOPREDIC
   CD3/CD28 signal sequence-containing CD19-CAR-T cells (CAR-T cells): provided by Division of Molecular therapy, The Institute of Medical Science, The University of Tokyo
   CD19-expressing K562 cell line (target cells): provided by Division of Molecular therapy, The Institute of Medical Science, The University of Tokyo
   Human Monocytes (monocytes): BIOPREDIC
   Lenti-X293T cells: Clontech
1.1.2 Reagents
   RPMI1640 medium: Thermo fisher (Gibco)
   Fetal Bovine Serum (FBS): Thermo fisher (Gibco)
   D-PBS(−): Wako Pure Chemical Industries, Ltd., Japan
   Disodium dihydrogen ethylenediamine tetraacetic acid dihydrate (EDTA): Junsei Chemical Co., Ltd., Japan
   Albumin from bovine serum (BSA): SIGMA
   Dimethyl Sulfoxide (DMSO): SIGMA
   Penicillin-Streptomycin-Glutamine: Thermo fisher
   2-Mercaptoethanol: SIGMA
   Trypan Blue Stain 0.4% (trypan blue solution): Thermo fisher (Gibco)
   1 mol/L HEPES Buffer Solution: Nacalai Tesque, Inc., Japan
   1 mol/L Sodium Hydroxide Solution: FUJIFILM Wako Pure Chemical Corporation
   CD4 MicroBeads human: Miltenyi Biotec
   CD8 MicroBeads human: Miltenyi Biotec
   CD14 MicroBeads human: Miltenyi Biotec
   MACS BSA Stock Solution: Miltenyi Biotec
   AutoMACS Rinsing Solution: Miltenyi Biotec
   Dynabeads Human T-Activator CD3/28 (T-cell stimulation beads): Thermo fisher (Gibco)
   Recombinant Human M-CSF: Pepro Tech
   Recombinant Human IFN-γ: Pepro Tech
   JTE-607 dihydrochloride (specified as the catalog name): Tocris Cat. No. 5185
   Prednisolone (PSL): Wako Pure Chemical Industries, Ltd., Japan, Cat. No. 165-11491
   Tocilizumab: absolute antibody Cat. No. L6529-1MG
   Lipopolysaccharides from *Escherichia coli* 055: B55 (LPS): SIGMA
   Adenosine 5′-triphosphate disodium salt hydrate (ATP): SIGMA
   Human IFN-γ DuoSet ELISA: R&D systems
   Human IL-6 DuoSet ELISA: R&D systems
   Human CCL2/MCP-1 DuoSet ELISA: R&D systems
   Human TNF-α DuoSet ELISA: R&D systems
   Human OPN DuoSet ELISA: R&D systems
   Human IL-1β DuoSet ELISA: R&D systems
   Human IL-18 DuoSet ELISA: R&D systems
   Human VEGF DuoSet ELISA: R&D systems
   Human IL-8 DuoSet ELISA: R&D systems
   DuoSet ELISA Ancillary Reagent Kit 2: R&D systems
   HQPlex Premixed Analyte Kit (multiplex assay): Bay bioscience
   In-Fusion HD cloning kit: Takara Bio Inc., Japan
1.1.3 Instruments
   MidiMACS Separator: Miltenyi Biotec
   MidiMACS-LS column (separatory column): Miltenyi Biotec
   Polypropylene conical tube (tube): FALCON
   Tissue Culture Plate, 96-well, Flat Bottom with Low Evaporate Lid (96-well plate): FALCON
1.1.4 Reagent solutions
   10% FBS RPMI (medium):
   RPMI1640 was supplemented with inactivated FBS (50 mL), Penicillin-Streptomycin-Glutamine (5 mL) and 0.1 M 2-Mercaptoethanol (250 µL) to give a total volume of 500 mL. The medium was stored at 4° C. and warmed to 37° C. in a thermostat before use.
   2 mM EDTA, 0.5% BSA-PBS (MACS Buffer):
   D-PBS(−) (44 mL) was supplemented with a 5% BSA solution (5 mL) and a 100 mM EDTA solution (1 mL). The prepared solution was stored at 4° C.
1.1.5 Devices
   Thermostat: Thermal ROBO TR-1A, AS ONE
   Centrifuge: AX-320, TOMY
   $CO_2$ incubator: MCO-170AICUVH, PANASONIC
   Plate reader: SPECTRAmax 384plus, Molecular Devices
   FACSVerse™ flow cytometer: Becton, Dickinson and Company
   EnSpire 2300: Perkin Elmer Japan 1.2 Methods
1.2.1 Effects of JTE-607 and PSL on T-Cell Stimulation Bead-Induced IFN-γ Production in CD8$^+$ T Cells Cryopreserved PBMCs were quickly thawed in a 37° C. thermostat and added to a tube containing medium. After centrifugation (at room temperature at 300 g for 10 minutes) to remove the supernatant, the cells were suspended in the medium, a portion of which was then mixed with a trypan blue solution to count the number of viable cells. The cell suspension was centrifuged (at room temperature at 300 g for 10 minutes) to remove the supernatant, followed by addition of MACS Buffer in a volume of 80 μL per $1 \times 10^7$ cells to suspend the cells, to which Human CD8 MicroBeads (20 μL) were further added. After being allowed to stand on ice for 15 minutes, the cell suspension was diluted with MACS Buffer (2 mL) and centrifuged (at room temperature at 300 g for 10 minutes) to remove the supernatant.

MACS Buffer (500 μL) was added to the tube, and the cells were suspended and then applied to a separatory column to separate CD8$^+$ cells. The CD8$^+$ cell fraction was diluted to 15 mL with the medium and then centrifuged (at room temperature at 300 g for 10 minutes). The supernatant was removed and the cells were suspended in the medium (1 mL), followed by counting the number of viable cells. The cell suspension adjusted with the medium to $1 \times 10^6$ cells/mL was seeded in a 96-well plate in a volume of 100 μL/well ($1 \times 10^5$ cells/well) and allowed to stand in a CO$_2$ incubator for 1 to 2 hours.

After addition of a 0.12% DMSO solution, a JTE-607 solution (final concentration: 10, 30, 100 and 300 nM) or a PSL solution (final concentration: 0.03, 0.3, 3 and 30 μM) in a volume of 50 μl/well, T-cell stimulation beads (10 μL/well; which corresponds to 2 μL of T-cell stimulation bead stock solution) and the medium (40 μL/well) were added and the cells were cultured in a CO$_2$ incubator for 3 days to collect the culture supernatants.

The collected culture supernatants were quantified for IFN-γ using Human IFN-γ DuoSet ELISA.

1.2.2 Effects of JTE-607 and PSL on LPS Stimulation-Induced IL-6 Production in CD14$^+$ Cells Cryopreserved PBMCs were quickly thawed in a 37° C. thermostat and added to a tube containing medium. After centrifugation (at room temperature at 300 g for 10 minutes) to remove the supernatant, the cells were suspended again in the medium, followed by counting the number of viable cells. The cell suspension was centrifuged (at room temperature at 300 g for 10 minutes) to remove the supernatant, followed by addition of MACS Buffer to suspend the cells, to which Human CD14 MicroBeads were further added. After being allowed to stand on ice for 15 minutes, the cell suspension was diluted with MACS Buffer and centrifuged (at room temperature at 300 g for 10 minutes) to remove the supernatant.

MACS Buffer was added to the tube, and the cells were suspended and then applied to a separatory column to separate CD14$^+$ cells. The CD14$^+$ cell fraction was diluted with the medium and then centrifuged (at room temperature at 300 g for 10 minutes). The supernatant was removed and the cells were suspended in the medium (1 mL), followed by counting the number of viable cells. The cell suspension was adjusted with the medium to $2.4 \times 10^5$ or $3 \times 10^5$ cells/mL and seeded in a 96-well plate ($2.4 \times 10^4$ cells/well), which was then allowed to stand in a CO$_2$ incubator for 1 to 2 hours.

After addition of a 0.12% DMSO solution, a JTE-607 solution (final concentration: 10, 30, 100 and 300 nM) or a PSL solution (final concentration: 0.03, 0.3, 3 and 30 μM), a LPS solution (final concentration: 3 ng/mL) was further added and the 96-well plate was allowed to stand in a CO$_2$ incubator for 3 days to collect the culture supernatants.

The collected culture supernatants were quantified for IL-6 using Human IL-6 DuoSet ELISA.

1.2.3 Effects of JTE-607 and PSL on LPS Stimulation-Induced IL-6 Production in PBMCs Cryopreserved PBMCs were quickly thawed in a 37° C. thermostat and added to a tube containing medium. After centrifugation (at room temperature at 300 g for 10 minutes) to remove the supernatant, the cells were suspended again in the medium (10 mL), followed by counting the number of viable cells. After centrifugation (at room temperature at 300 g for 10 minutes) to remove the supernatant, the medium was added to suspend the cells at $1 \times 10^6$ cells/mL. This cell suspension was seeded in a 96-well plate in a volume of 100 μL/well ($1 \times 10^5$ cells/well). After addition of a 0.12% DMSO solution, a JTE-607 solution (final concentration: 10, 30, 100 and 300 nM) or a PSL solution (final concentration: 0.03, 0.3, 3 and 30 μM) in a volume of 30 μL/well, a LPS solution was added in a volume of 5 μl/well (final concentration: 3 ng/mL). The cells were cultured in a CO$_2$ incubator for 3 days to collect the culture supernatants.

The collected culture supernatants were quantified for IL-6 using Human IL-6 DuoSet ELISA.

1.2.4 Effects of JTE-607 and PSL on an Evaluation System for T-Cell Stimulation Bead- and LPS Stimulation-Induced CRS Toxicity in PBMCs Cryopreserved PBMCs were quickly thawed in a 37° C. thermostat and added to a tube containing medium. After centrifugation (at room temperature at 300 g for 10 minutes) to remove the supernatant, the cells were suspended again in the medium (10 mL), followed by counting the number of viable cells. After centrifugation (at room temperature at 300 g for 10 minutes) to remove the supernatant, the medium was added to suspend the cells at $1 \times 10^6$ cells/mL. This cell suspension was seeded in a 96-well plate in a volume of 100 μl/well ($1 \times 10^5$ cells/well) and allowed to stand in a CO$_2$ incubator for 1 to 2 hours.

After addition of a 0.12% DMSO solution, a JTE-607 solution (final concentration: 10, 30, 100 and 300 nM) or a PSL solution (final concentration: 0.03, 0.3, 3 and 30 μM) in a volume of 50 μL/well, T-cell stimulation beads (10 μL/well; which corresponds to 2 μL of T-cell stimulation bead stock solution) and a LPS solution (final concentration: 3 ng/mL; 40 μl/well) were added. The cells were cultured in a CO$_2$ incubator for 3 days to collect the culture supernatants.

The collected culture supernatants were quantified for IFN-γ and IL-6 using Human IFN-γ DuoSet ELISA and Human IL-6 DuoSet ELISA.

1.2.5 Effects of JTE-607 and PSL on an Evaluation System for T-Cell Stimulation Bead- and LPS Stimulation-Induced CRS Toxicity in CD4$^+$ T Cell-Depleted PBMCs Cryopreserved human PBMCs were quickly thawed in a 37° C. thermostat and added to a tube containing medium. After centrifugation (at room temperature at 300 g for 10 minutes) to remove the supernatant, the cells were suspended again in the medium (10 mL), followed by counting the number of viable cells. The remainder of the cell suspension was centrifuged (at room temperature at 300 g for 10 minutes) to remove the supernatant, followed by addition of MACS Buffer in a volume of 80 μL and Human CD4 MicroBeads in a volume of 20 μL per $1 \times 10^7$ cells to suspend the cells. After being allowed to stand on ice for 15 minutes, the cell suspension was diluted with MACS Buffer (2 mL) and centrifuged (at room temperature at 300 g for 10 minutes) to remove the supernatant. MACS Buffer (500 μL)

was added to the tube, and the cells were suspended and then applied to a separatory column to separate CD4⁻ cells (a pass-through fraction of CD4⁺ cells). The CD4⁻ cell fraction was diluted to 15 mL with the medium and then centrifuged (at room temperature at 300 g for 10 minutes) to remove the supernatant, and the cells were then suspended again in the medium (1 mL), followed by counting the number of viable cells. The cell suspension adjusted with the medium to 1×10⁶ cells/mL was seeded in a 96-well plate in a volume of 100 µl/well (1×10⁵ cells/well) and allowed to stand in a CO₂ incubator for 1 to 2 hours.

After addition of a 0.12% DMSO solution, a JTE-607 solution (final concentration: 10, 30, 100 and 300 nM) or a PSL solution (final concentration: 0.03, 0.3, 3 and 30 µM) in a volume of 50 µL/well, T-cell stimulation beads (10 µL/well; which corresponds to 2 µL of T-cell stimulation bead stock solution) and a LPS solution (final concentration: 3 ng/mL; 40 µL/well) were added and the cells were cultured in a CO₂ incubator for 3 days to collect the culture supernatants.

The collected culture supernatants were quantified for IFN-γ and IL-6 using Human IFN-γ DuoSet ELISA and Human IL-6 DuoSet ELISA.

1.2.6 Effects of JTE-607 and PSL on LPS Stimulation-Induced MCP-1 Production in CD14⁺ Cells Cryopreserved PBMCs were quickly thawed in a 37° C. thermostat and added to a tube containing medium. After centrifugation (at room temperature at 300 g for 10 minutes) to remove the supernatant, the cells were suspended again in the medium, followed by counting the number of viable cells. The cell suspension was centrifuged (at room temperature at 300 g for 10 minutes) to remove the supernatant, followed by addition of MACS Buffer to suspend the cells, to which Human CD14 MicroBeads were further added. After being allowed to stand on ice for 15 minutes, the cell suspension was diluted with MACS Buffer and centrifuged (at room temperature at 300 g for 10 minutes) to remove the supernatant.

MACS Buffer was added to the tube, and the cells were suspended and then applied to a separatory column to separate CD14⁺ cells. The CD14⁺ cell fraction was diluted with the medium and then centrifuged (at room temperature at 300 g for 10 minutes). The supernatant was removed and the cells were suspended in the medium (1 mL), followed by counting the number of viable cells. The cell suspension was adjusted with the medium to 2.4×10⁵ or 3×10⁵ cells/mL and seeded in a 96-well plate (2.4×10⁴ cells/well), which was then allowed to stand in a CO₂ incubator for 1 to 2 hours.

After addition of a 0.12% DMSO solution, a JTE-607 solution (final concentration: 10, 30, 100 and 300 nM) or a PSL solution (final concentration: 0.03, 0.3, 3 and 30 µM), a LPS solution (final concentration: 3 ng/mL) was further added and the 96-well plate was allowed to stand in a CO₂ incubator for 3 days to collect the culture supernatants.

The collected culture supernatants were quantified for MCP-1 using Human CCL2/MCP-1 DuoSet ELISA.

1.2.7 Effects of JTE-607 and PSL on T-Cell Stimulation Bead-Induced TNF-α Production in CD8⁺ T Cells The culture supernatants collected in 1.2.1 were quantified for TNF-α using Human TNF-α DuoSet ELISA.

1.2.8 Effects of JTE-607 and PSL on LPS Stimulation-Induced TNF-α Production in CD14⁺ Cells The culture supernatants collected in 1.2.2 were quantified for TNF-α using Human TNF-α DuoSet ELISA.

1.2.9 Effects of JTE-607 and PSL on LPS Stimulation-Induced TNF-α Production in PBMCs The culture supernatants collected in 1.2.2 were quantified for TNF-α using Human TNF-α DuoSet ELISA.

1.2.10 Effects of JTE-607, PSL and Tocilizumab on LPS Stimulation-Induced OPN Production in CD14⁺ Cells Cryopreserved PBMCs were quickly thawed in a 37° C. thermostat and added to a tube containing medium. After centrifugation (at room temperature at 300 g for 10 minutes) to remove the supernatant, the cells were suspended again in the medium, followed by counting the number of viable cells. The cell suspension was centrifuged (at room temperature at 300 g for 10 minutes) to remove the supernatant, followed by addition of MACS Buffer to suspend the cells, to which Human CD14 MicroBeads were further added. After being allowed to stand on ice for 15 minutes, the cell suspension was diluted with MACS Buffer and centrifuged (at room temperature at 300 g for 10 minutes) to remove the supernatant. MACS Buffer was added to the tube, and the cells were suspended and then applied to a separatory column to separate CD14⁺ cells. The CD14⁺ cell fraction was diluted with the medium and then centrifuged (at room temperature at 300 g for 10 minutes). The supernatant was removed and the cells were suspended in the medium (1 mL), followed by counting the number of viable cells. The cell suspension was adjusted with the medium to 2.4×10⁵ or 3×10⁵ cells/mL and seeded in a 96-well plate (2.4×10⁴ cells/well), which was then allowed to stand in a CO₂ incubator for 1 to 2 hours.

After addition of a 0.12% DMSO solution, a JTE-607 solution (final concentration: 10, 30, 100 and 300 nM), a PSL solution (final concentration: 0.03, 0.3, 3 and 30 µM) or tocilizumab (final concentration: 10, 100 and 1000 ng/mL), a LPS solution (final concentration: 500 ng/mL) was further added and the 96-well plate was allowed to stand in a CO₂ incubator for 3 days to collect the culture supernatants.

The collected culture supernatants were quantified for OPN using Human OPN DuoSet ELISA.

1.2.11 Effects of JTE-607, PSL and Tocilizumab on LPS Stimulation-Induced IL-1β Production in CD14⁺ Cells The culture supernatants collected in 1.2.10 were quantified for IL-1β using Human IL-1β DuoSet ELISA.

1.2.12 Effects of JTE-607, PSL and Tocilizumab on ATP Stimulation-Induced IL-18 Production from LPS-Pretreated CD14⁺ Cells Cryopreserved PBMCs were quickly thawed in a 37° C. thermostat and added to a tube containing medium. After centrifugation (at room temperature at 300 g for 10 minutes) to remove the supernatant, the cells were suspended again in the medium, followed by counting the number of viable cells. The cell suspension was centrifuged (at room temperature at 300 g for 10 minutes) to remove the supernatant, followed by addition of MACS Buffer to suspend the cells, to which Human CD14 MicroBeads were further added. After being allowed to stand on ice for 15 minutes, the cell suspension was diluted with MACS Buffer and centrifuged (at room temperature at 300 g for 10 minutes) to remove the supernatant.

MACS Buffer was added to the tube, and the cells were suspended and then applied to a separatory column to separate CD14⁺ cells. The CD14⁺ cell fraction was diluted with the medium and then centrifuged (at room temperature at 300 g for 10 minutes). The supernatant was removed and the cells were suspended in the medium (1 mL), followed by counting the number of viable cells. The cell suspension adjusted with the medium to 2×10⁶ cells/mL was seeded in a 96-well plate (1×10⁵ cells/well) and allowed to stand in a CO₂ incubator for 1 to 2 hours. The CD14⁺ cells (1×10⁵ cells/well) were seeded in a 96-well flat bottom plate, followed by addition of a 0.12% DMSO solution, a JTE-607 solution (final concentration: 10, 30, 100 and 300 nM), a PSL solution (final concentration: 0.03, 0.3, 3 and 30 µM) or tocilizumab (final concentration: 10, 100 and 1000 ng/mL) and incubation for 30 minutes at 37° C. The cells were then stimulated with LPS (final concentration: 500 ng/mL) for 6 hours at 37° C. and an ATP solution (final concentration: 5 mM) was added thereto, and the 96-well plate was further allowed to stand in a $CO_2$ incubator for 2 hours to collect the culture supernatants.

The collected culture supernatants were quantified for IL-18 using Human IL-18 DuoSet ELISA.

1.2.13 Effects of JTE-607, PSL and Tocilizumab on LPS Stimulation-Induced VEGF Production in Macrophages CD14$^+$ cells were cultured in 20 ng/mL M-CSF-containing RPMI medium at 37° C. for 5 days to induce differentiation into macrophages (during which the medium was replaced once every two days with fresh 20 ng/mL M-CSF-containing RPMI medium). The macrophages were seeded in a 96-well plate at 5×10$^5$ cells/mL, followed by addition of a JTE-607 solution (final concentration: 10, 30, 100 and 300 nM), a PSL solution (final concentration: 0.03, 0.3, 3 and 30 µM) or tocilizumab (final concentration: 10, 100 and 1000 ng/mL) and incubation at 37° C. for 30 minutes. The macrophages were then stimulated with LPS (final concentration: 100 ng/mL) or RPMI medium alone at 37° C. for 3 days, followed by collecting the culture supernatants. The collected culture supernatants were quantified for VEGF using Human VEGF DuoSet ELISA.

1.2.14 Effect of CD14$^+$ Cells on the Killer Activity of CAR-T Cells

FMC63 scFv, the hinge, transmembrane and cytoplasmic domains of CD28 and the cytoplasmic domain of CD3-ζ were used to construct anti-CD19 CAR on the basis of the method of Kochenderfer, et al.[15]. The sequence was obtained from GenBank (HM852952) and an IDT codon optimization tool (http://sg.igtdna.com/CodonOpt) was used to remove BamHI recognition sequences within FMC63. The optimized FMC63-28z sequence was chemically synthesized and amplified by polymerase chain reaction (PCR) with the following primer set.

```
                                        (SEQ ID NO: 1)
5'-CGCTACCGTCGTCGAATTCGCCGCCACCATGCTTC-3'
```

```
                                        (SEQ ID NO: 2)
5'-GAAGTTCGTGCTCCGGGATCCCGCGAGGGGGCAG-3'
```

The PCR product was inserted into the multicloning site (EcoRI and BamHI) of lentivirus plasmid CSII-EF-MCS-2A-eGFP by using an In-Fusion HD cloning kit to obtain CSII-EF-FMC63-28z-2A-eGFP. To prepare a lentivirus vector, CSII-EF-FMC63-28z-2A-eGFP and a packaging plasmid (pMDLg/p.RRE, pRSV-rev and pMD.G) were co-transfected into Lenti-X293T cells. The prepared lentivirus vector was infected into peripheral blood mononuclear cells stimulated with anti-CD3 antibody, anti-CD28 antibody and IL-2, followed by FACS sorting to obtain a CD3-positive and eGFP-positive fraction as CAR-T cells.

On the basis of the method of Kochenderfer, et al.[15], the open reading frame of human CD19 was synthesized and amplified by PCR with the following primers.

```
                                        (SEQ ID NO: 3)
5'-ccggttcgaattcgccatATGCCACCTCCCGCCTC-3'
```

```
                                        (SEQ ID NO: 4)
5'-cgatgttaactctagatcaCCTGGGTGCTCCAGGTGC-3'
```

The PCR product was inserted into lentivirus backbone plasmid CSII-EF-MCS via the EcoRI and XbaI sites by using an In-Fusion HD cloning kit to obtain CSII-EF-hCD19. In addition, to prepare a firefly luciferase (fLuc) expression plasmid, fLuc cDNA was amplified by PCR with the following primer set using the pmirGLO plasmid (Promega) as a template.

```
                                        (SEQ ID NO: 5)
5'-GAATTCGCCACCATGGAAGATGCCAA-3'
```

```
                                        (SEQ ID NO: 6)
5'-GGATCCCACGGCGATCTTGCCGCC-3'
```

The PCR product was cleaved with EcoRI and BamHI and then inserted into the multicloning site of CSII-EF-MCS-2A-eGFP to obtain CSII-EF-fLuc-2A-eGFP. To prepare a lentivirus vector, CSII-EF-hCD19 or CSII-EF-fLuc-2A-eGFP and a packaging plasmid (pMDLg/p.RRE, pRSV-rev and pMD.G) were co-transfected into Lenti-X293T cells. The prepared lentivirus vectors were infected into K562 cells, followed by FACS sorting to obtain a CD19- and eGFP-positive fraction as target cells.

The target cells (3×10$^3$ cells/well) were seeded in a 96-well plate, to which the CAR-T cells were then added to give an E/T ratio of 0, 0.1, 0.3, 1, 3 and 10. This culture system was incubated for 3 days under conditions where CD14$^+$ cells (1.5×10$^4$ cells/well) were added or not added thereto. Subsequently, luciferase activity was determined by detection of emission intensity with an EnSpire 2300.

1.2.15 Effect of CD14$^+$ Cells on Cytokine Production in a Mixed Culture System Using CAR-T Cells CAR-T cells (5×10$^4$ cells/well) and target cells (1×10$^4$ cells/well) were seeded in a 96-well plate and incubated under conditions where CD14$^+$ cells (1×10$^4$ cells/well) were added or not added thereto. The supernatants were collected at 0, 4, 24, 48 and 72 hours after the initiation of culture, and IFN-γ, TNF-α, MCP-1, IL-6 and IL-4 in each supernatant were measured by FACS multiplex assay.

1.2.16 Effects of JTE-607 and PSL on the Killer Activity of CAR-T Cells

CAR-T cells (5×10$^4$ cells/well), target cells (1×10$^4$ cells/well) and CD14$^+$ cells (5×10$^4$ cells/well) were seeded in a 96-well plate, to which a JTE-607 solution (final concentration: 0.1, 1, 10, 100 and 1000 nM) or a PSL solution (final concentration: 0.1, 1, 10 and 100 µM) was then added, followed by incubation for 2 days. Subsequently, luciferase activity was determined by detection of emission intensity with an EnSpire 2300.

1.2.17 Effects of JTE-607, PSL and Tocilizumab in a CRS Toxicity Evaluation System Using CAR-T Cells CAR-T cells (1.5×10$^4$ cells/well), target cells (3×10$^3$ cells/well) and monocytes (1.5×10$^4$ cells/well) were seeded in a 96-well plate, to which a JTE-607 solution (final concentration: 1, 10, 100 and 1000 nM), a PSL solution (final concentration: 0.1, 1, 10 and 100 µM) or a tocilizumab solution (final concentration: 0.1, 1, 10 and 100 µg/mL) was then added, followed by incubation. The supernatants were collected at 72 hours after the initiation of culture, and various cytokines in each supernatant were measured by FACS multiplex assay.

Figure 1:
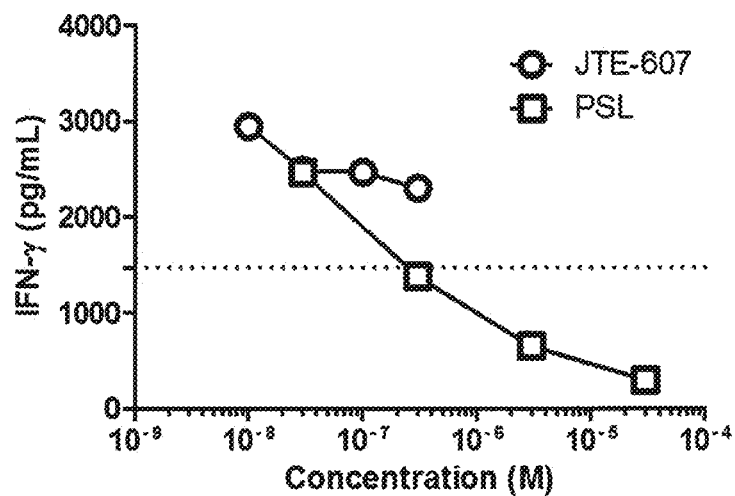
FIG. 1 shows the effects of JTE-607 and PSL on T-cell stimulation bead-induced IFN-γ production in CD8+ T cells.
Figure 3:
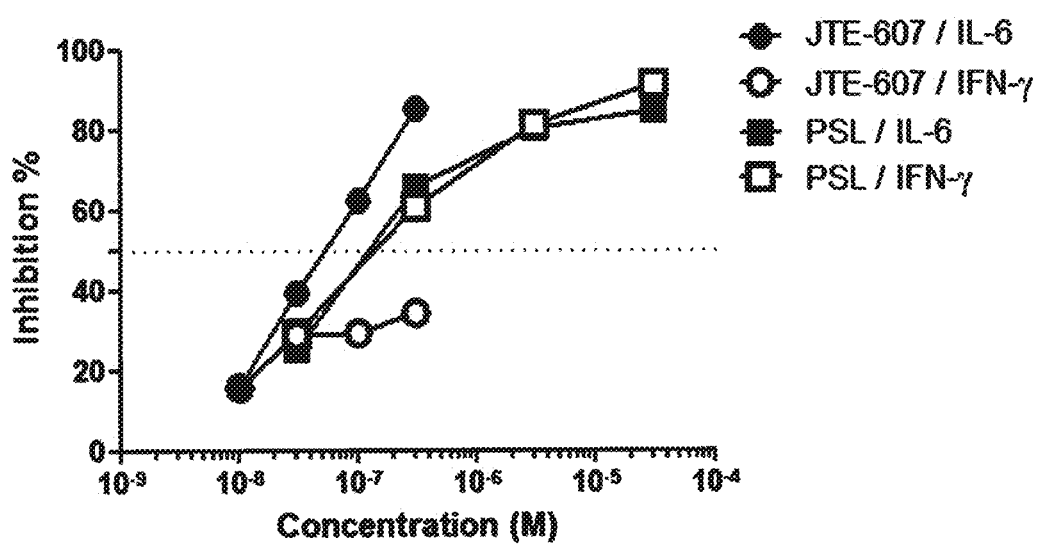
FIG. 3 shows the effects of JTE-607 and PSL on IFN-γ production from CD8+ T cells and IL-6 production from CD14+ cells.

1.3 Results
1.3.1 Effects of JTE-607 and PSL on T-Cell Stimulation Bead-Induced IFN-γ and Other Cytokine Production in CD8+ T Cells JTE-607 showed no significant suppressive effect on IFN-γ production from CD8+ T cells stimulated with T-cell stimulation beads ($IC_{50}$ value=>300 nM). On the other hand, PSL suppressed this IFN-γ production in a concentration-dependent manner ($IC_{50}$ value=0.1494 μM). JTE-607 was found to have a weak direct effect on CD8+ T cells (FIG. 1, FIG. 3 and Table 1).

TABLE 1

Inhibitory activity of JTE-607 and PSL on various cytokine production in different culture systems

| Cells used | Stimulation | Parameters measured | $IC_{50}$ value JTE-607 | $IC_{50}$ value PSL |
|---|---|---|---|---|
| CD8+ T cells | CD3/CD28 | IFN-γ | >300 nM | 0.149 μM |
| | | TNF-α | 231 nM | 0.035 μM |
| CD14+ cells | LPS | IL-6 | 52.9 nM | 0.151 μM |
| | | MCP-1 | 21.3 nM | 6.598 μM |
| | | OPN | 132.1 nM | >30 μM |
| | | TNF-α | >300 nM | 0.042 μM |
| | | IL-1β | 3.45 nM | >30 μM |
| CD14+ cells/ CD8+ T cells | — | Ratio (IL-6/IFN-γ) | <0.18 | 1.01 |
| PBMCs | LPS | IL-6 | 17.7 nM | 0.176 μM |
| | | TNF-α | 30.7 nM | 0.073 μM |
| PBMCs | CD3/CD28 + LPS | IFN-γ | 50.1 nM | 0.053 μM |
| | | IL-6 | 40.4 nM | 3.569 μM |
| | | Ratio (IL-6/IFN-γ) | 0.81 | 67.3 |
| CD4+ T cell-depleted PBMCs | CD3/CD28 + LPS | IFN-γ | 80.9 nM | 0.042 μM |
| | | IL-6 | 42.2 nM | >30 μM |
| | | Ratio (IL-6/IFN-γ) | 0.52 | >714 |
| CD14+ cells (LPS-pretreated) | ATP | IL-18 | 2.40 nM | >30 μM |
| Macrophages | LPS | VEGF | 204.3 nM | <0.030 μM |

Figure 2:
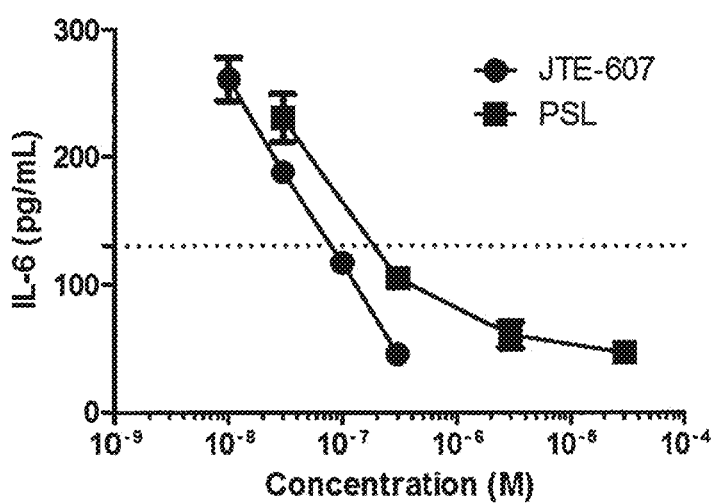
FIG. 2 shows the effects of JTE-607 and PSL on LPS stimulation-induced IL-6 production in CD14+ cells.

1.3.2 Effects of JTE-607 and PSL on LPS Stimulation-Induced IL-6 Production in CD14+ Cells JTE-607 and PSL were evaluated for their effect on IL-6 production from CD14+ cells. JTE-607 and PSL both showed suppressive activity and had $IC_{50}$ values of 52.9 nM and 0.151 μM, respectively. As previously reported, JTE-607 was found to have an effect on myeloid lineage cells (FIG. 2, FIG. 3 and Table 1).

Figure 4:
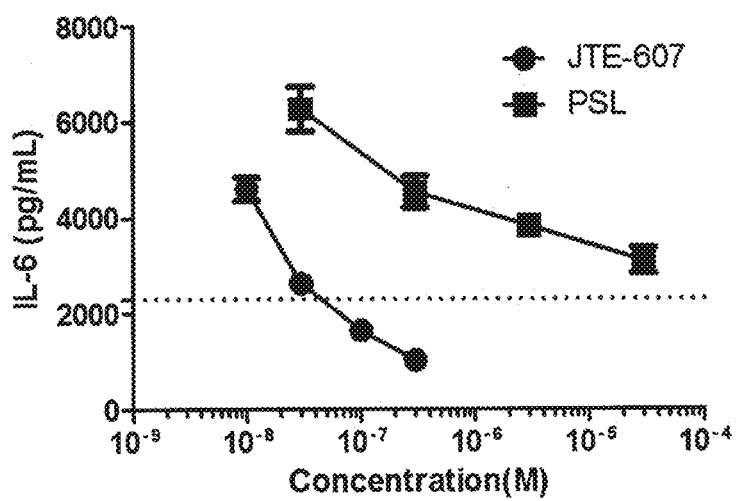
FIG. 4 shows the effects of JTE-607 and PSL on LPS stimulation-induced IL-6 production in peripheral blood mononuclear cells (PBMCs).

1.3.3 Effects of JTE-607 and PSL on LPS Stimulation-Induced IL-6 Production in PBMCs JTE-607 and PSL were evaluated for their effect on IL-6 production from PBMCs. JTE-607 and PSL both showed suppressive activity and had $IC_{50}$ values of 17.7 nM and 0.176 μM, respectively (FIG. 4 and Table 1).

Figure 5:
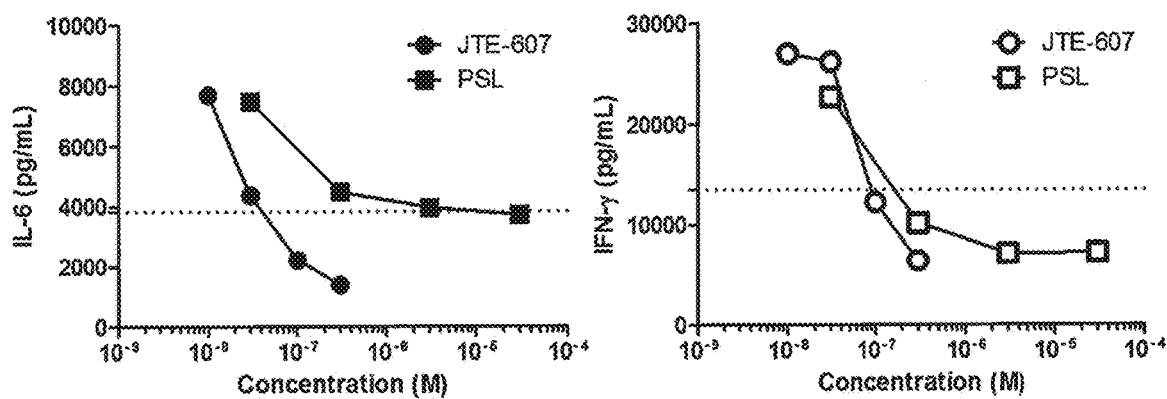
FIG. 5 shows the effects of JTE-607 and PSL on T-cell stimulation bead- and LPS stimulation-induced IL-6 and IFN-γ production in PBMCs.
Figure 6:
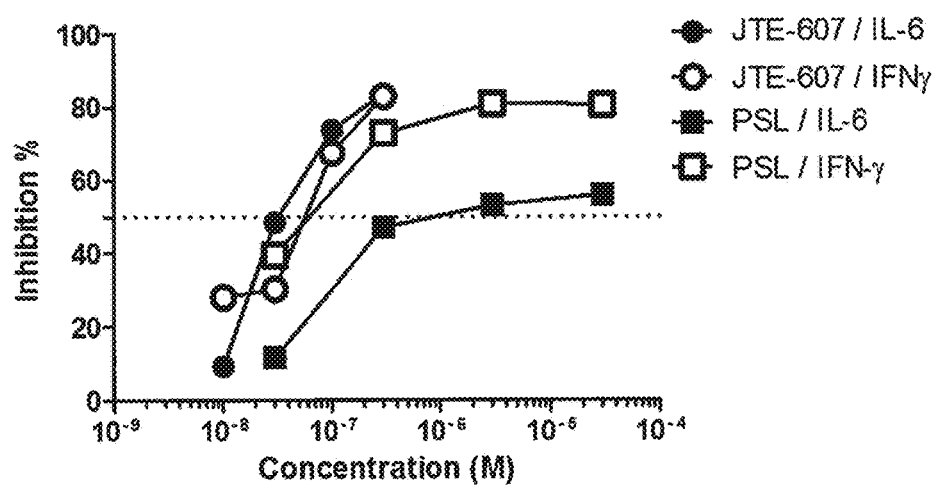
FIG. 6 shows the effects of JTE-607 and PSL on an evaluation system for T-cell stimulation bead- and LPS stimulation-induced CRS toxicity in PBMCs.

1.3.4 Effects of JTE-607 and PSL on an Evaluation System for T-Cell Stimulation Bead- and LPS Stimulation-Induced CRS Toxicity in PBMCs JTE-607 and PSL were evaluated for their effect on IL-6 and IFN-γ production from PBMCs co-stimulated with T-cell stimulation beads and LPS. JTE-607 suppressed the co-stimulated IL-6 and IFN-γ production in a concentration-dependent manner and had $IC_{50}$ values of 40.4 nM for IL-6 and 50.1 nM for IFN-γ. Moreover, the ratio of $IC_{50}$ values for IL-6 and IFN-γ (ratio) was 0.81. On the other hand, PSL more strongly suppressed IFN-γ production than IL-6 production. JTE-607 was found to be different from PSL which strongly acts on T cell functions (FIG. 5, FIG. 6 and Table 1).

Figure 7:
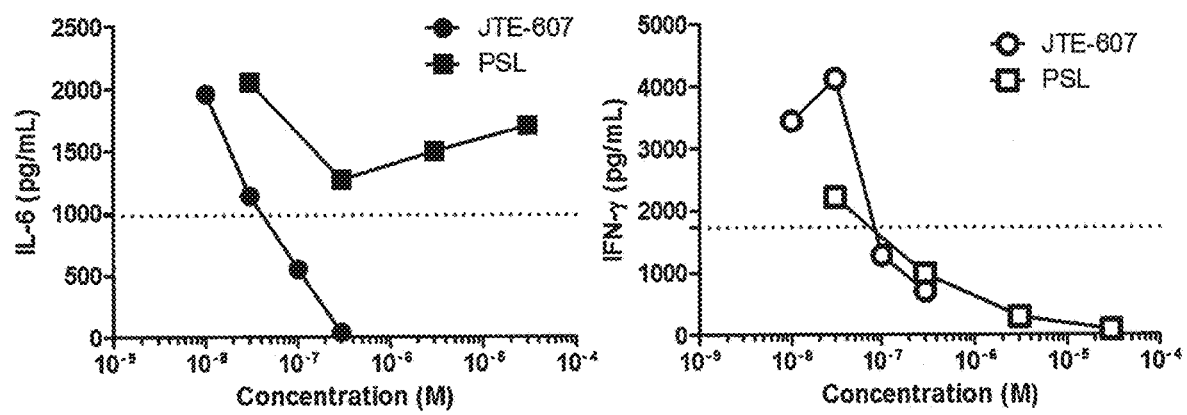
FIG. 7 shows the effects of JTE-607 and PSL on T-cell stimulation bead- and LPS stimulation-induced IL-6 and IFN-γ production in CD4+ T cell-depleted PBMCs.
Figure 8:
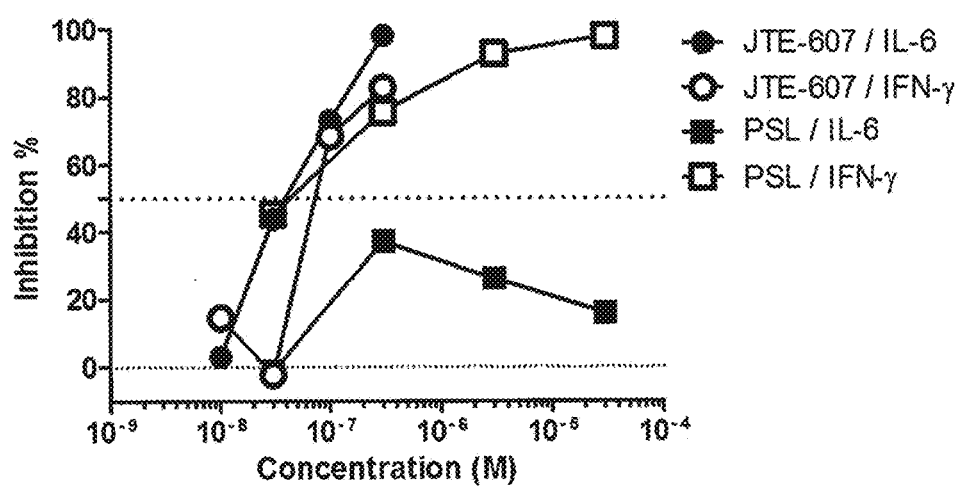
FIG. 8 shows the effects of JTE-607 and PSL on an evaluation system for T-cell stimulation bead- and LPS stimulation-induced CRS toxicity in CD4+ T cell-depleted PBMCs.

1.3.5 Effects of JTE-607 and PSL on an Evaluation System for T-Cell Stimulation Bead- and LPS Stimulation-Induced CRS Toxicity in CD4+ T Cell-Depleted PBMCs To clarify the involvement of CD4+ T cells in the system co-stimulated with T-cell stimulation beads and LPS, CD4+ T cell-depleted PBMCs (i.e., PBMCs processed to remove CD4+ T cells) were used to evaluate the effects of JTE-607 and PSL. JTE-607 suppressed the co-stimulated IL-6 and IFN-γ production in a concentration-dependent manner and had similar $IC_{50}$ values for both ($IC_{50}$ value for IL-6=42.2 nM, $IC_{50}$ value for IFN-γ=80.9 nM). Moreover, the ratio of $IC_{50}$ values for IL-6 and IFN-γ (ratio) was 0.52, and JTE-607 showed an effect directed rather toward IL-6 production inhibition. On the other hand, PSL suppressed IFN-γ production in a concentration-dependent manner ($IC_{50}$ value=0.042 μM) but did not suppress IL-6 production (FIG. 7, FIG. 8 and Table 1). Similar results were able to be obtained in the studies using PBMCs and CD4+ T cell-depleted PBMCs, thus suggesting that the involvement of CD4+ T cells in the system co-stimulated with T-cell stimulation beads and LPS would be low.

Figure 9:
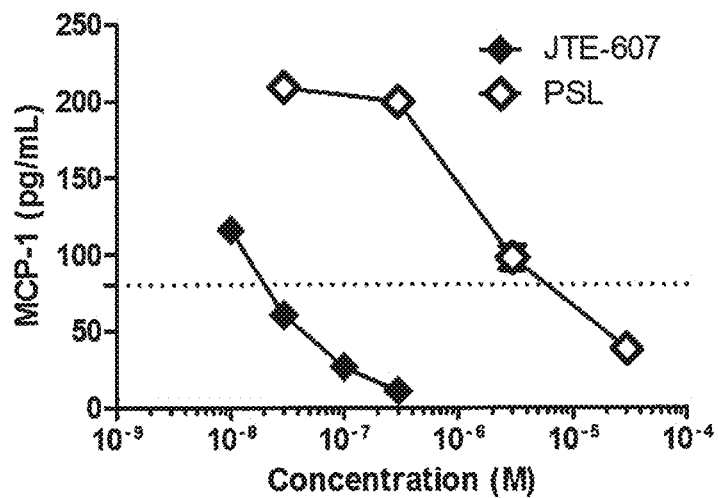
FIG. 9 shows the effects of JTE-607 and PSL on LPS stimulation-induced MCP-1 production in PBMCs.

1.3.6 Effects of JTE-607 and PSL on LPS Stimulation-Induced MCP-1 Production in CD14+ Cells JTE-607 and PSL were evaluated for their effect on MCP-1 production from CD14+ cells. JTE-607 and PSL both showed suppressive activity and had $IC_{50}$ values of 21.3 nM and 6.598 μM, respectively. JTE-607 was suggested to exert a strong inhibitory effect on macrophage activation through MCP-1 production inhibition (FIG. 9 and Table 1).

Figure 10:
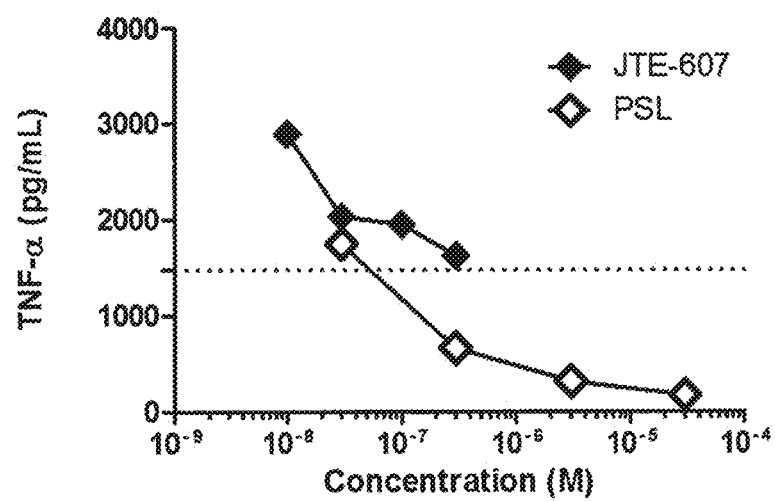
FIG. 10 shows the effects of JTE-607 and PSL on T-cell stimulation bead-induced TNF-α production in CD8+ T cells.

1.3.7 Effects of JTE-607 and PSL on T-Cell Stimulation Bead-Induced TNF-α Production in CD8+ T Cells JTE-607 was found to have a weaker suppressive effect on TNF-α production from CD8+ T cells stimulated with T-cell stimulation beads ($IC_{50}$ value=231.4 nM) when compared to the suppressive effect of PSL ($IC_{50}$ value=0.0348 μM) (FIG. 10 and Table 1).

Figure 11:
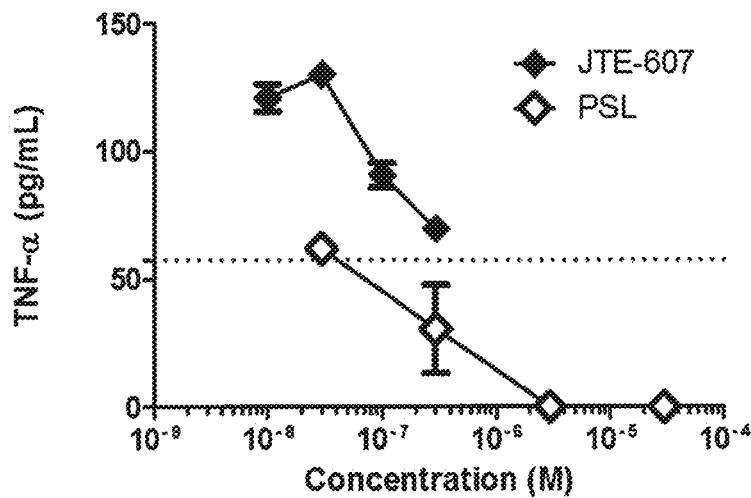
FIG. 11 shows the effects of JTE-607 and PSL on LPS stimulation-induced TNF-α production in CD14+ cells.

1.3.8 Effects of JTE-607 and PSL on LPS Stimulation-Induced TNF-α Production in CD14+ Cells PSL was found to have a suppressive effect on TNF-α production from CD14+ cells stimulated with LPS ($IC_{50}$ value=0.0417 μM). On the other hand, JTE-607 showed a suppressive effect in a manner dependent on its concentration added, but its $IC_{50}$ value was not able to be calculated. In general, it has been known that TNF-α production from CD14+ cells transiently increases from immediately after stimulation. The measurement was made under evaluation conditions optimal for gradually increasing cytokines such as IL-6, and the culture supernatants used in this measurement were therefore evaluated under conditions where the production level of TNF-α was reduced, so that JTE-607 would not show any clear suppression (FIG. 11 and Table 1).

Figure 12:
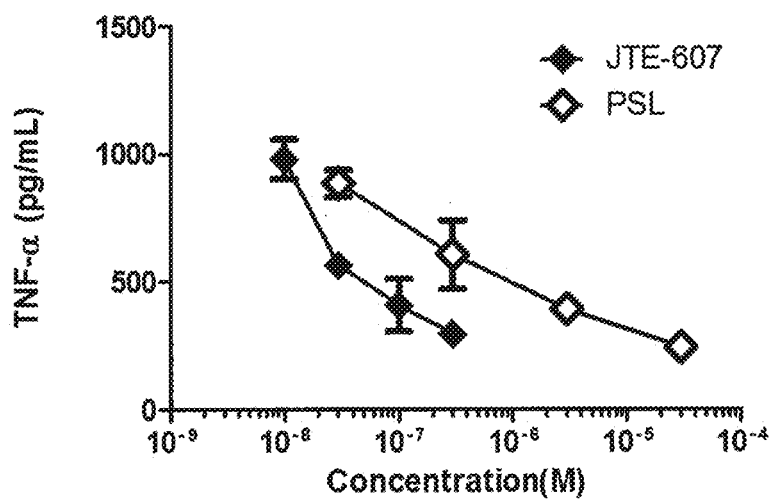
FIG. 12 shows the effects of JTE-607 and PSL on LPS stimulation-induced TNF-α production in PBMCs.

1.3.9 Effects of JTE-607 and PSL on LPS Stimulation-Induced TNF-α Production in PBMCs JTE-607 and PSL both showed suppressive activity and had $IC_{50}$ values of 30.7 nM and 0.073 μM, respectively (FIG. 12 and Table 1). In PBMCs containing various cells, these cells mutually stimulate each other to allow continuous production. For this reason, JTE-607 would show a suppressive effect.

Figure 13:
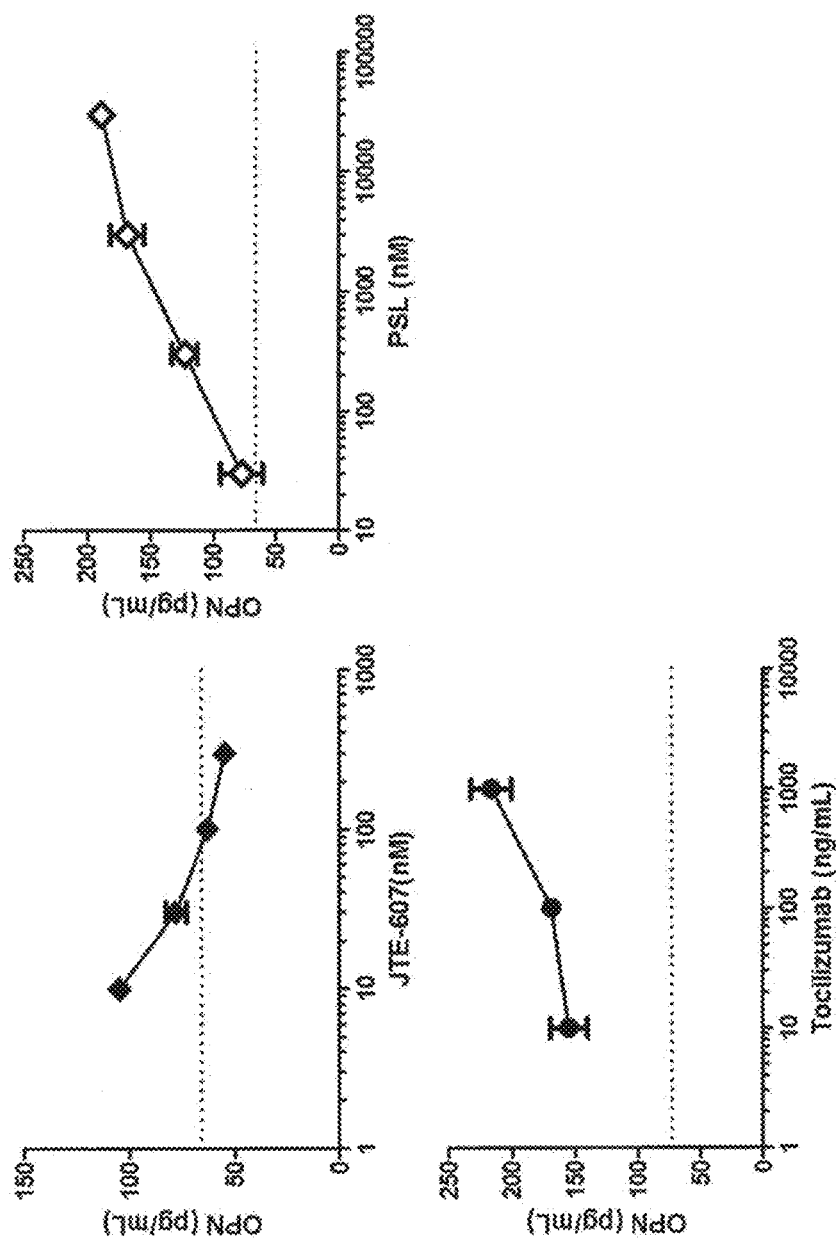
FIG. 13 shows the effects of JTE-607, PSL and tocilizumab on LPS stimulation-induced OPN production in PBMCs.

1.3.10 Effects of JTE-607, PSL and Tocilizumab on LPS Stimulation-Induced OPN Production in CD14+ Cells JTE-607, PSL and tocilizumab were evaluated for their effect on OPN production from CD14+ cells. JTE-607 showed suppressive activity and had an $IC_{50}$ value of 132.1 nM. On the other hand, PSL and tocilizumab both showed no suppressive effect on OPN production (FIG. 13 and Table 1). JTE-607 was suggested to inhibit osteoclast activation seen in LCH lesions through OPN production inhibition.

Figure 14:
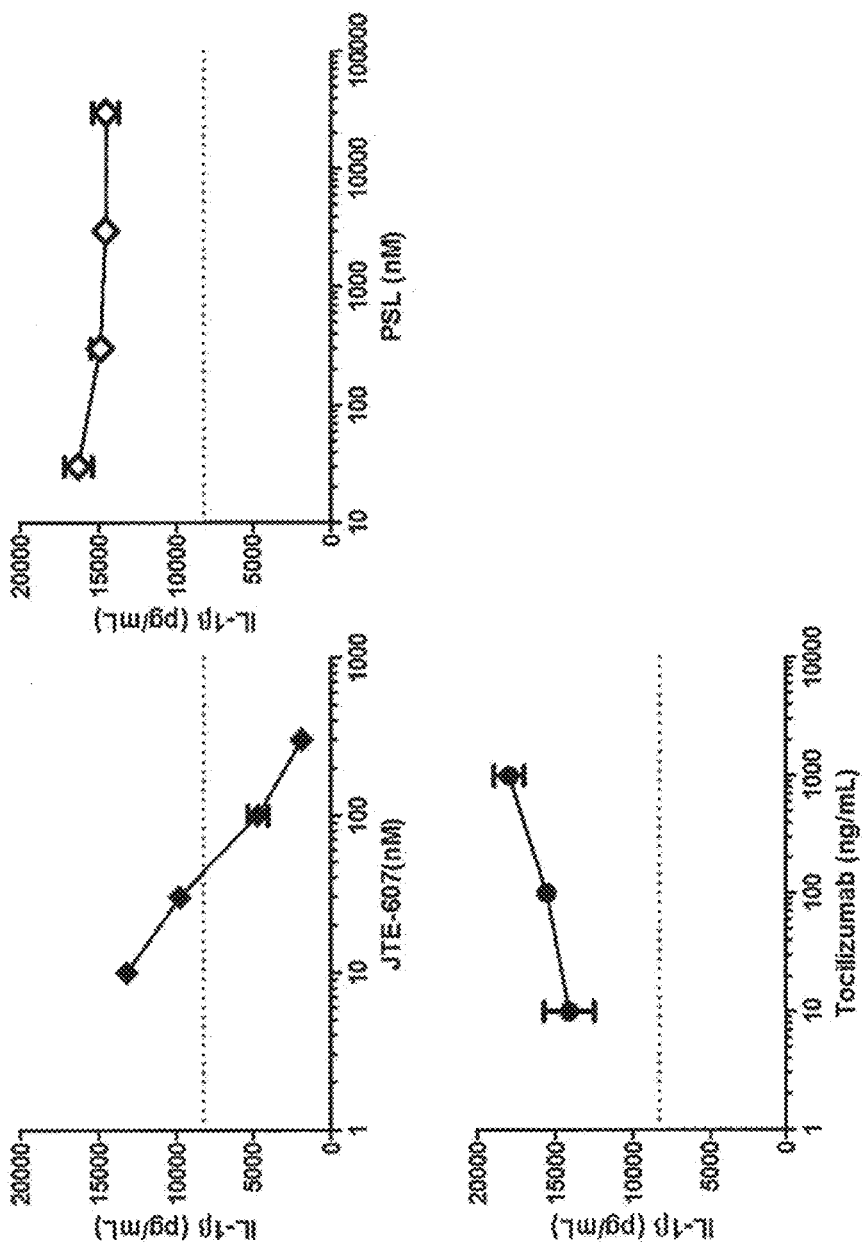
FIG. 14 shows the effects of JTE-607, PSL and tocilizumab on LPS stimulation-induced IL-1β production in PBMCs.

1.3.11 Effects of JTE-607, PSL and Tocilizumab on LPS Stimulation-Induced IL-13 Production in $CD14^+$ Cells JTE-607 showed suppressive activity on IL-1β production and had an $IC_{50}$ value of 3.45 nM. On the other hand, PSL and tocilizumab both showed no suppressive effect on IL-1β production (FIG. 14 and Table 1). JTE-607 was suggested to have a different effect from that of existing drugs such as PSL and tocilizumab.

Figure 15:
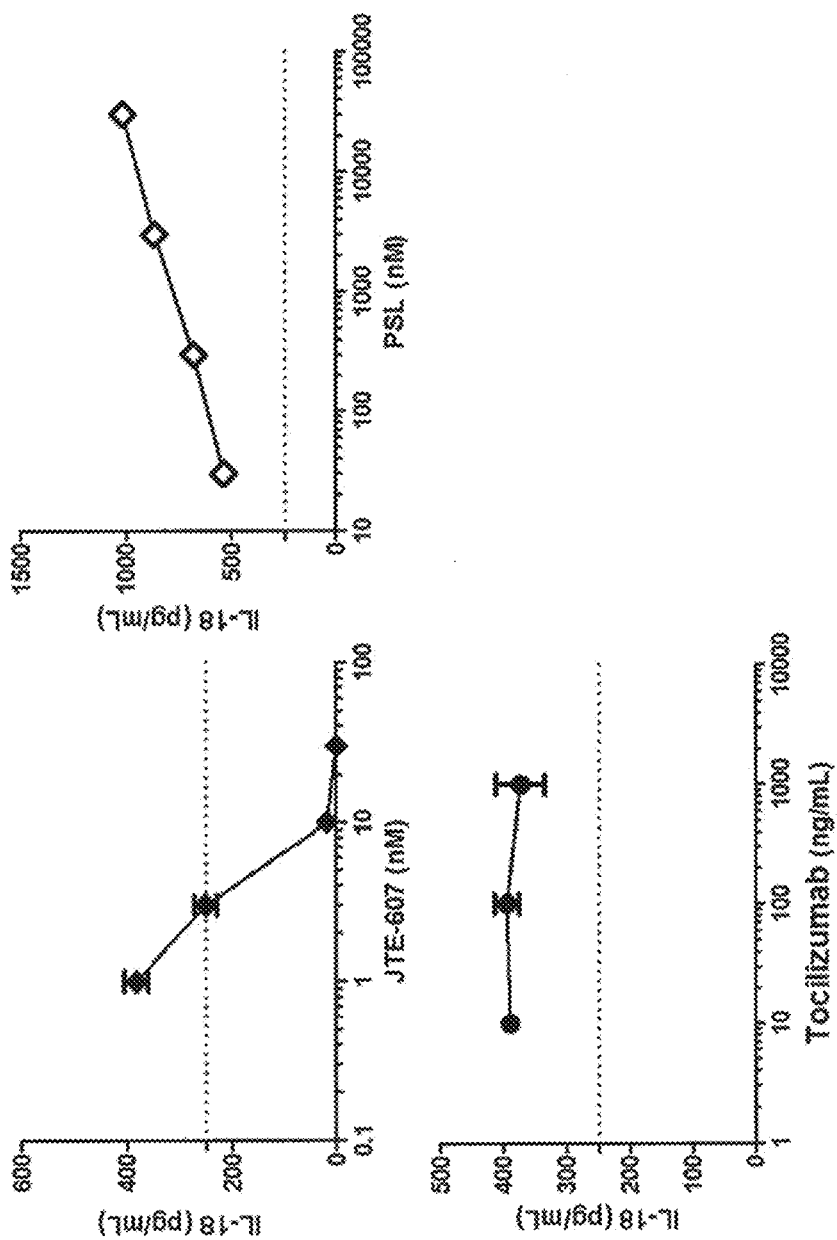
FIG. 15 shows the effects of JTE-607, PSL and tocilizumab on ATP stimulation-induced IL-18 production in LPS-pretreated CD14+ cells.

1.3.12 Effects of JTE-607, PSL and Tocilizumab on ATP Stimulation-Induced IL-18 Production from LPS-Pretreated $CD14^+$ Cells JTE-607, PSL and tocilizumab were evaluated for their effect on IL-18 production from LPS-pretreated $CD14^+$ cells. JTE-607 showed suppressive activity and had an $IC_{50}$ value of 2.40 nM. On the other hand, PSL and tocilizumab both showed no suppressive effect on IL-18 production (FIG. 15 and Table 1). JTE-607 was suggested to inhibit IL-18 production to thereby ameliorate pathological conditions in a group of diseases characterized by high IL-18 production. IL-18 is an inflammatory cytokine whose production is maintained high independently of IL-6, and JTE-607 was suggested to have an effect on an inflammatory pathological condition masked upon tocilizumab administration.

Figure 16:
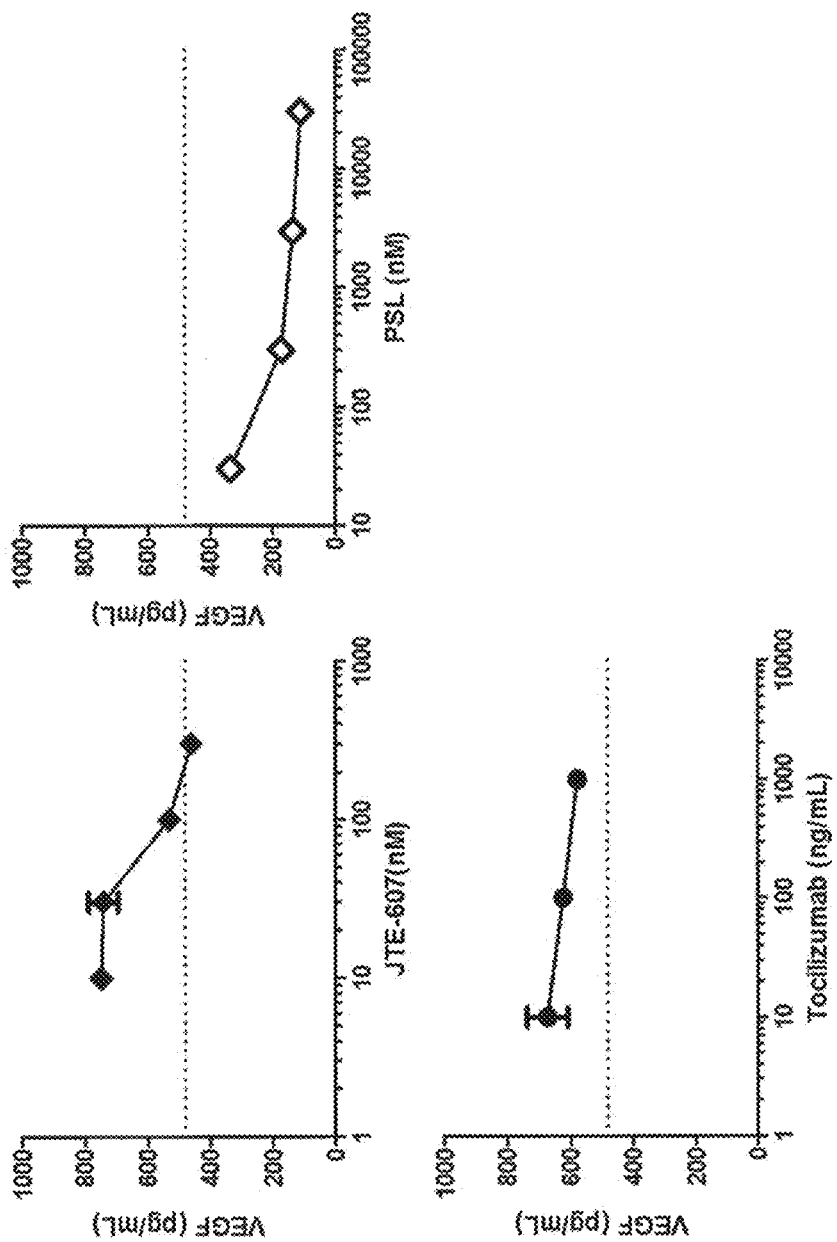
FIG. 16 shows the effects of JTE-607, PSL and tocilizumab on LPS stimulation-induced VEGF production in macrophages.

1.3.13 Effects of JTE-607, PSL and Tocilizumab on LPS Stimulation-Induced VEGF Production in Macrophages PSL showed a strong effect on VEGF production from macrophages, and its $IC_{50}$ value was not able to be calculated because 50% or more inhibition was observed even at the lowest evaluation concentration, i.e., 30 nM. On the other hand, JTE-607 tended to suppress VEGF production from macrophages, but its effect was marginal. Tocilizumab showed no suppressive effect on VEGF production (FIG. 16 and Table 1).

Figure 17:
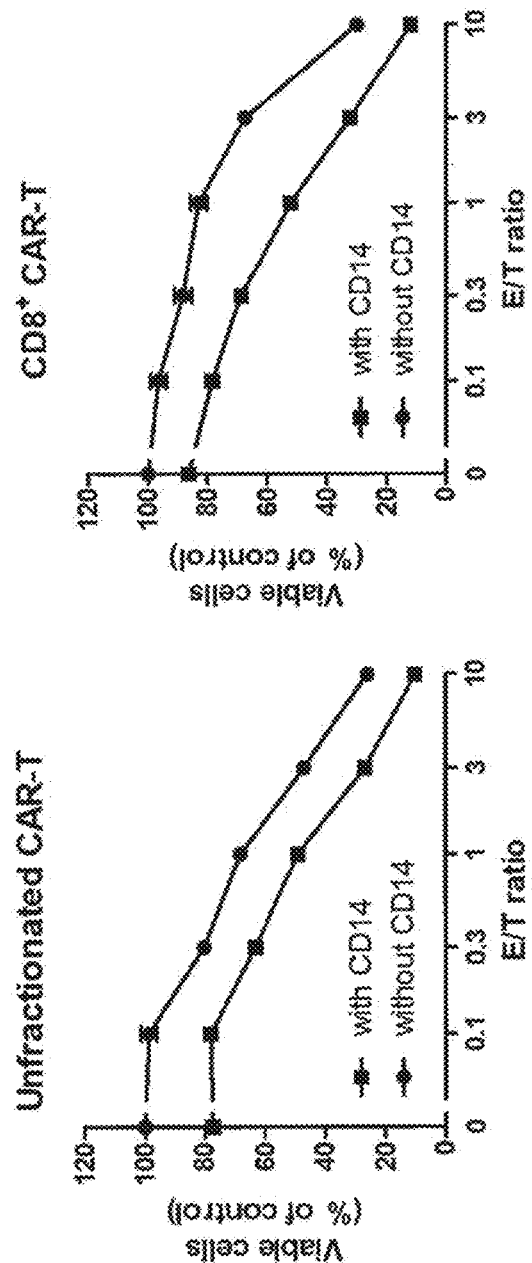
FIG. 17 shows the effect of CD14+ cells on the killer activity of CAR-T cells.

1.3.14 In Vitro Evaluation System for CRS Toxicity Originating from Cancer Cell Recognition by CAR-T Cells To detect cytokine release leading to CRS toxicity, a culture system for target cell recognition by CAR-T cells (killer activity) and a culture system further containing peripheral blood $CD14^+$ cells were compared with each other. The killer activity on target cells was elevated in culture with $CD14^+$ cells when compared to culture without $CD14^+$ cells (FIG. 17).

Figure 18:
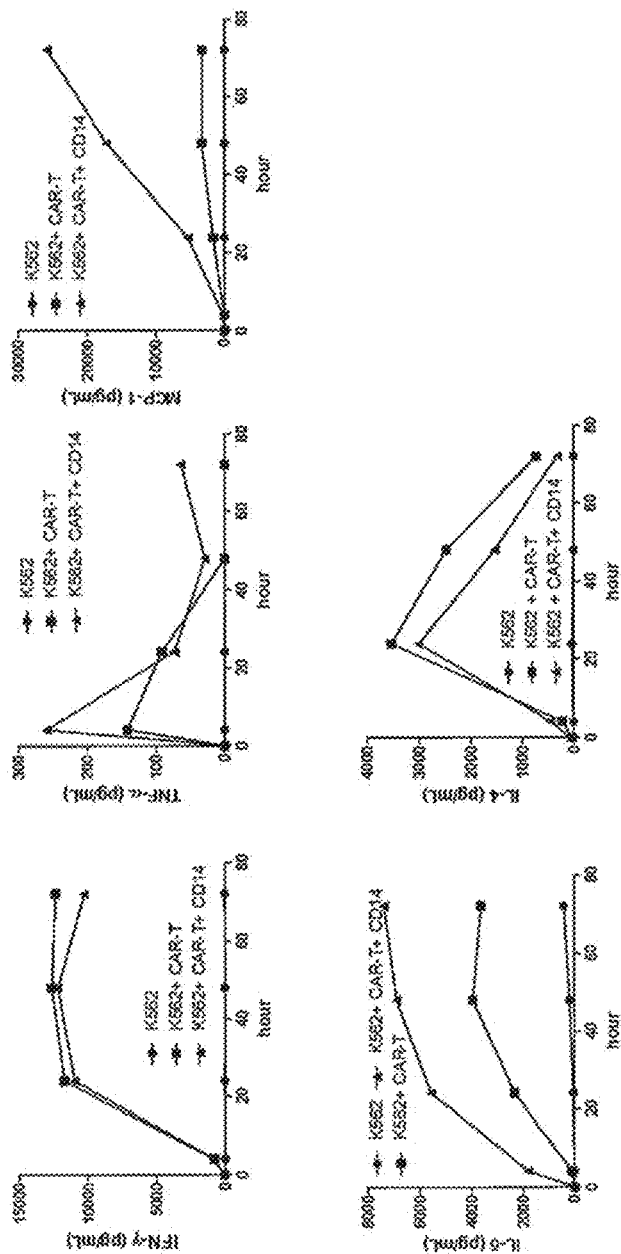
FIG. 18 shows the effect of CD14+ cells on cytokine production in a mixed culture system using CAR-T cells.

Subsequently, the production of various cytokines in culture with and without $CD14^+$ cells was quantified overtime. There was no great difference in the production of IFN-γ, a cytokine derived from CAR-T cells. On the other hand, in the production of IL-6 and MCP-1, a several-fold to 10-fold or more difference was observed in each case, and this result would reflect that the activation state of $CD14^+$ cells was significant (FIG. 18). Incidentally, IL-6 and MCP-1 have both been reported as biomarkers for predicting and determining the severity of CRS toxicity[16]. In view of the foregoing, such a mixed culture system of three types of cells, i.e., "CAR-T cells, target cells and $CD14^+$ cells" would be an in vitro culture system allowing simultaneous evaluation of "target cancer cell killer activity" and "CRS toxicity" in CAR-T cell therapy.

1.3.15 Effects of JTE-607 and PSL on the Killer Activity of CAR-T Cells

Figure 19:
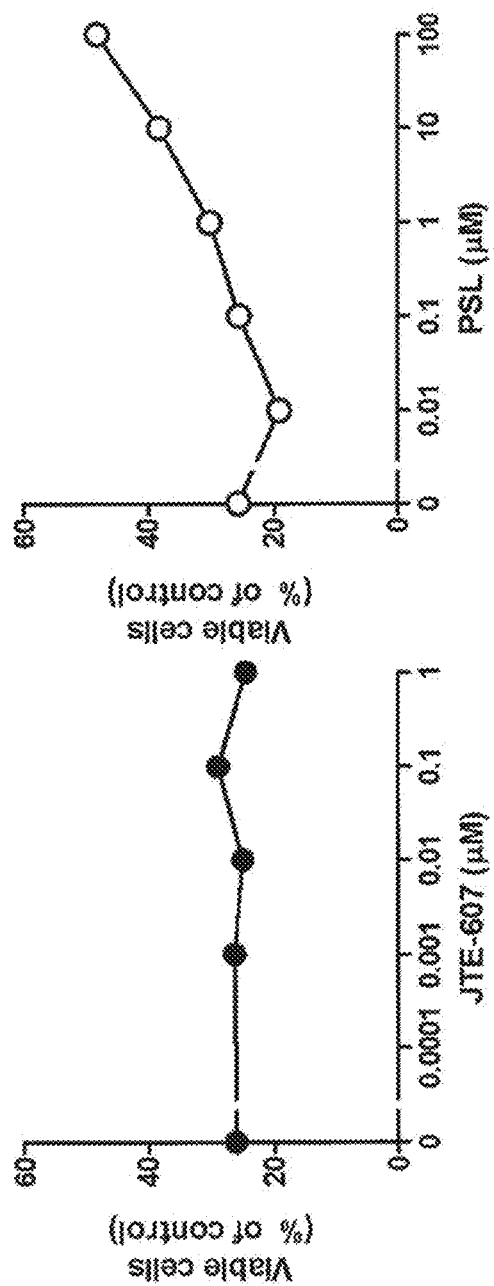
FIG. 19 shows the effects of JTE-607 and PSL on the killer activity of CAR-T cells.

PSL showed a suppressive effect on the killer activity of CAR-T cells in a concentration-dependent manner, whereas JTE-607 did not affect the killer activity of CAR-T cells (FIG. 19).

Figure 20:
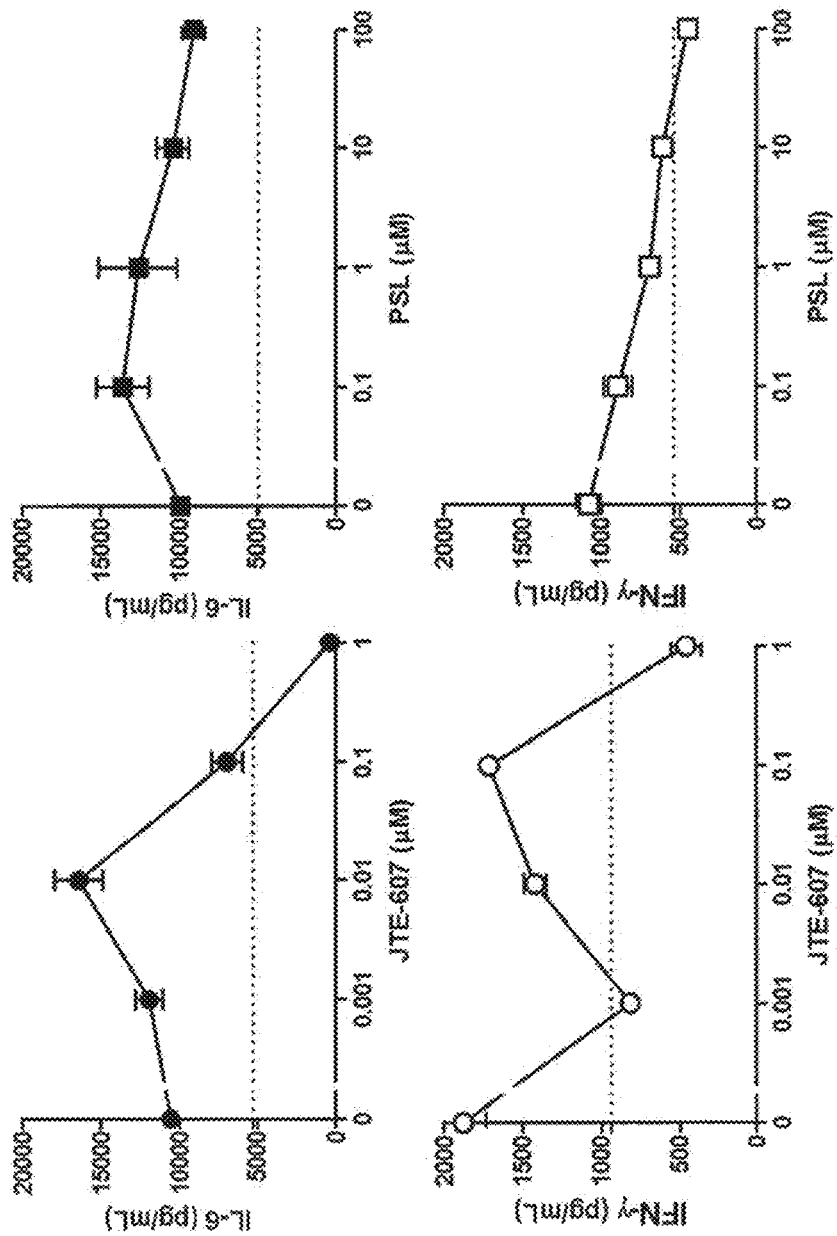
FIG. 20 shows the effects of JTE-607 and PSL on IL-6 and IFN-γ production in a CRS toxicity evaluation system using CAR-T cells.
Figure 21:
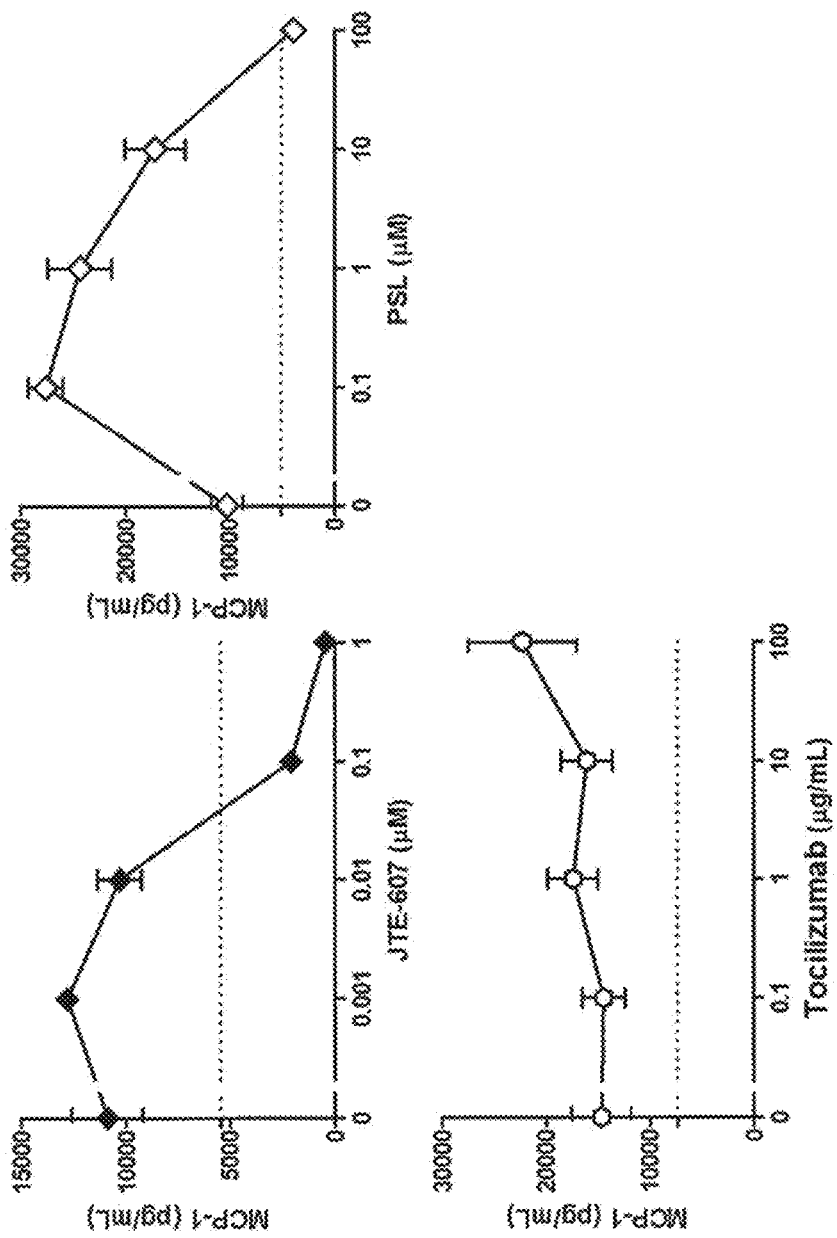
FIG. 21 shows the effects of JTE-607, PSL and tocilizumab on MCP-1 production in a CRS toxicity evaluation system using CAR-T cells.
Figure 22:
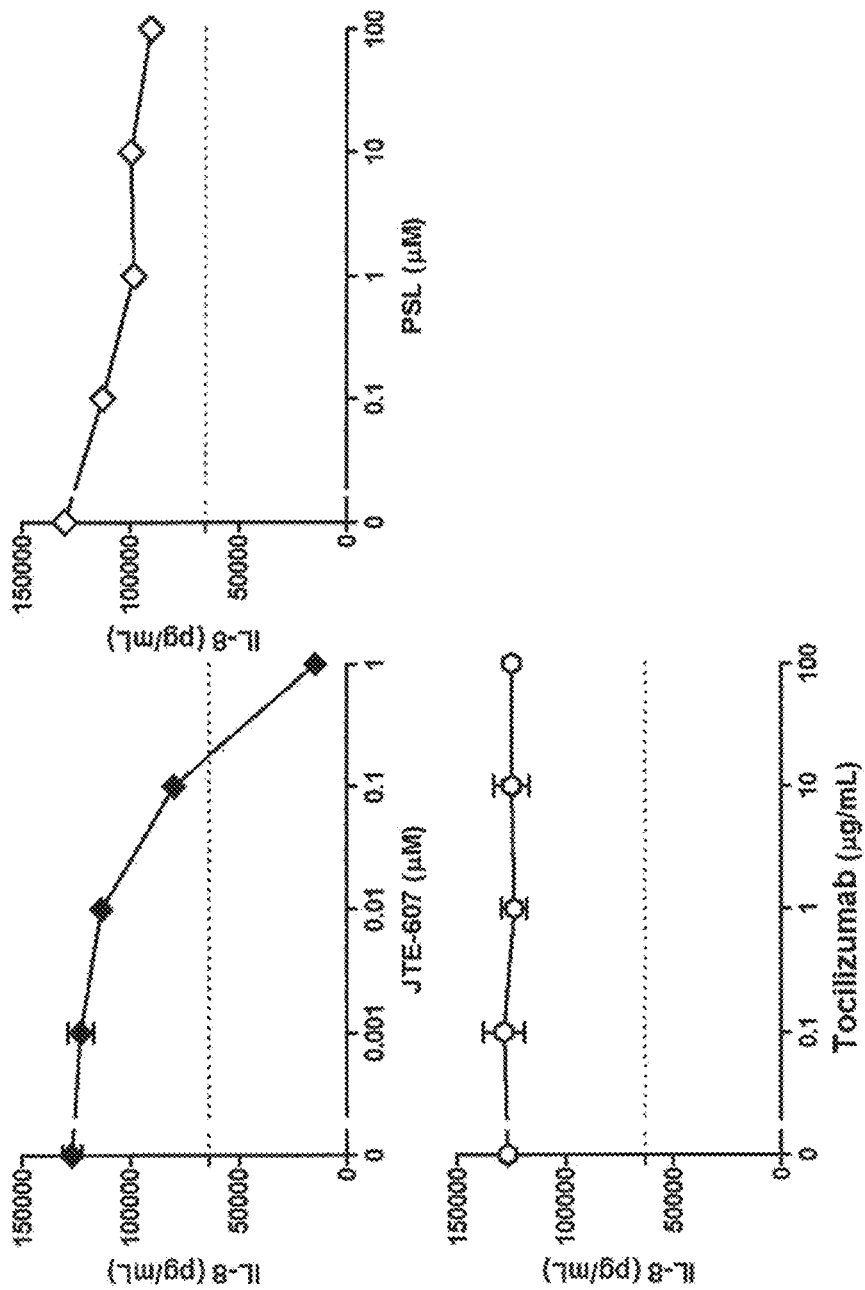
FIG. 22 shows the effects of JTE-607, PSL and tocilizumab on IL-8 production in a CRS toxicity evaluation system using CAR-T cells.
Figure 23:
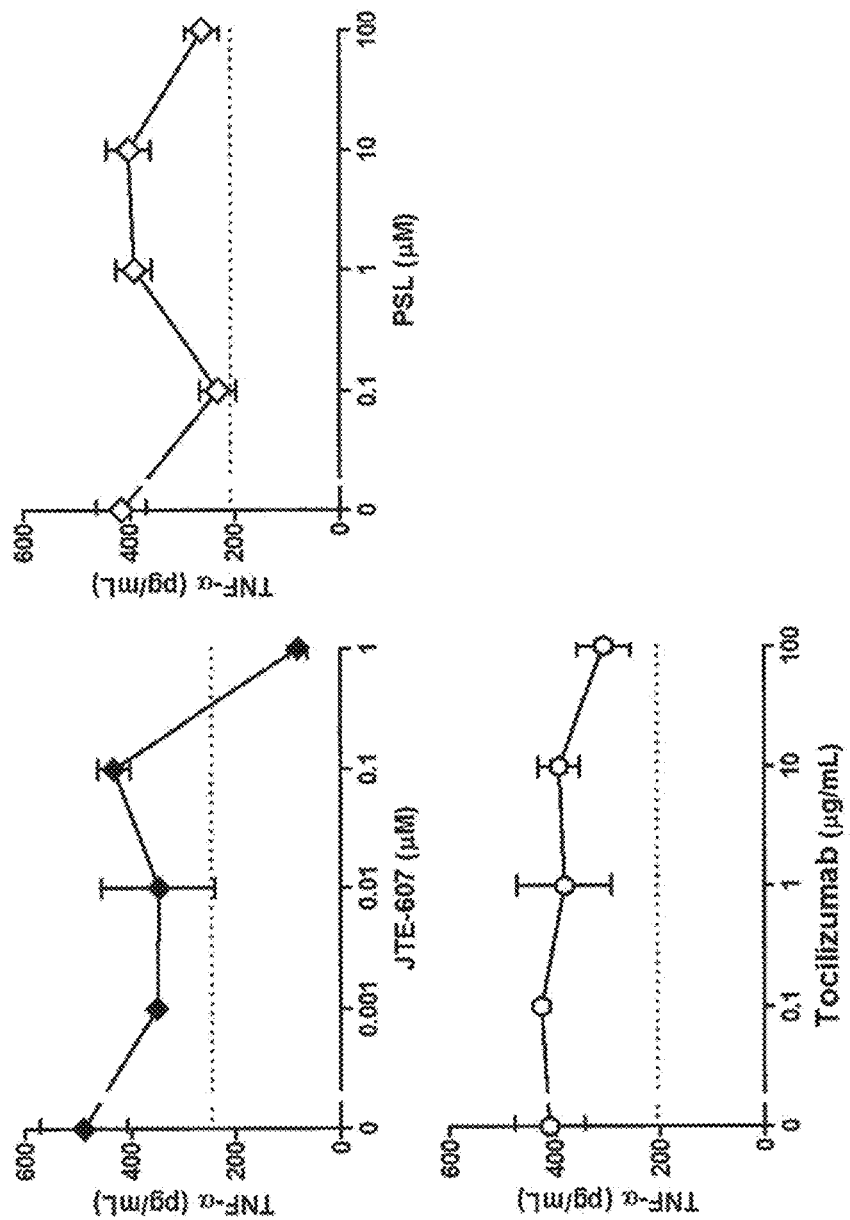
FIG. 23 shows the effects of JTE-607, PSL and tocilizumab on TNF-α production in a CRS toxicity evaluation system using CAR-T cells.
Figure 24:
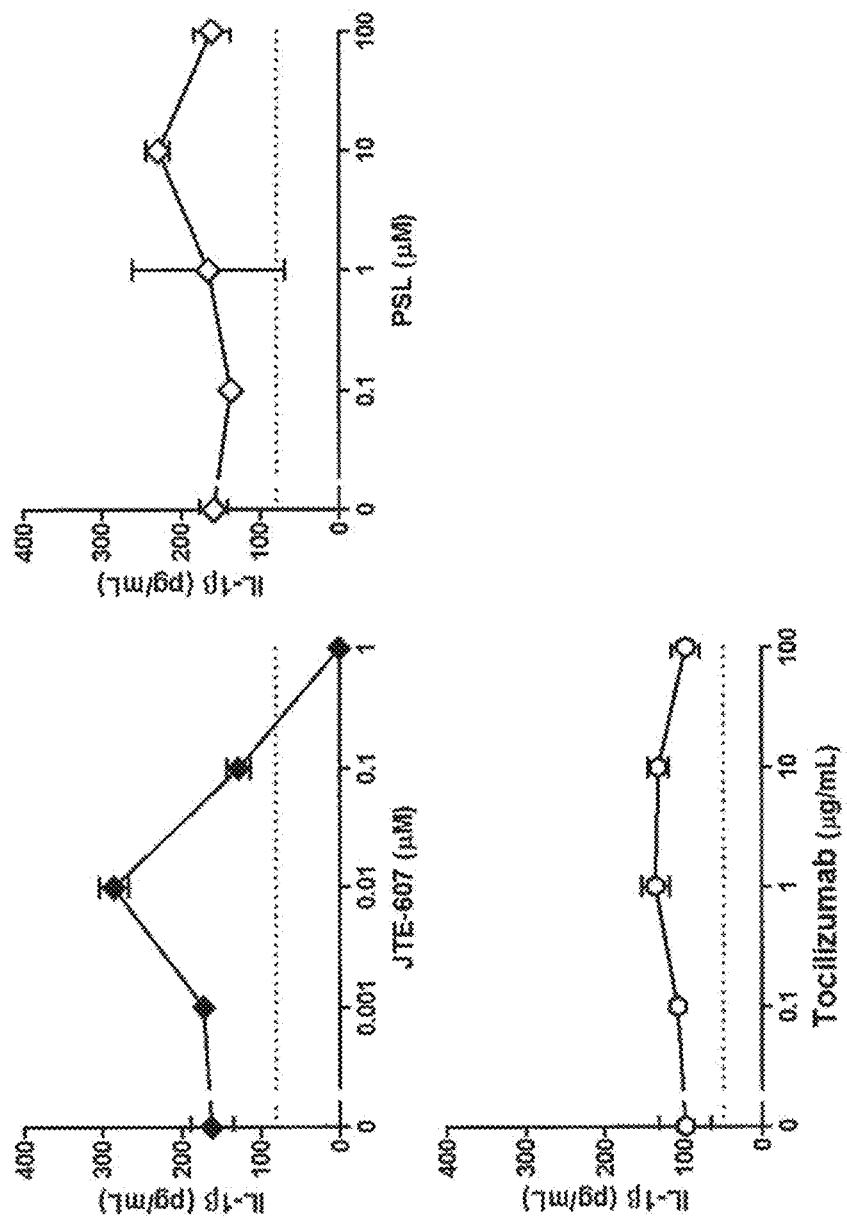
FIG. 24 shows the effects of JTE-607, PSL and tocilizumab on IL-1β production in a CRS toxicity evaluation system using CAR-T cells.
Figure 25:
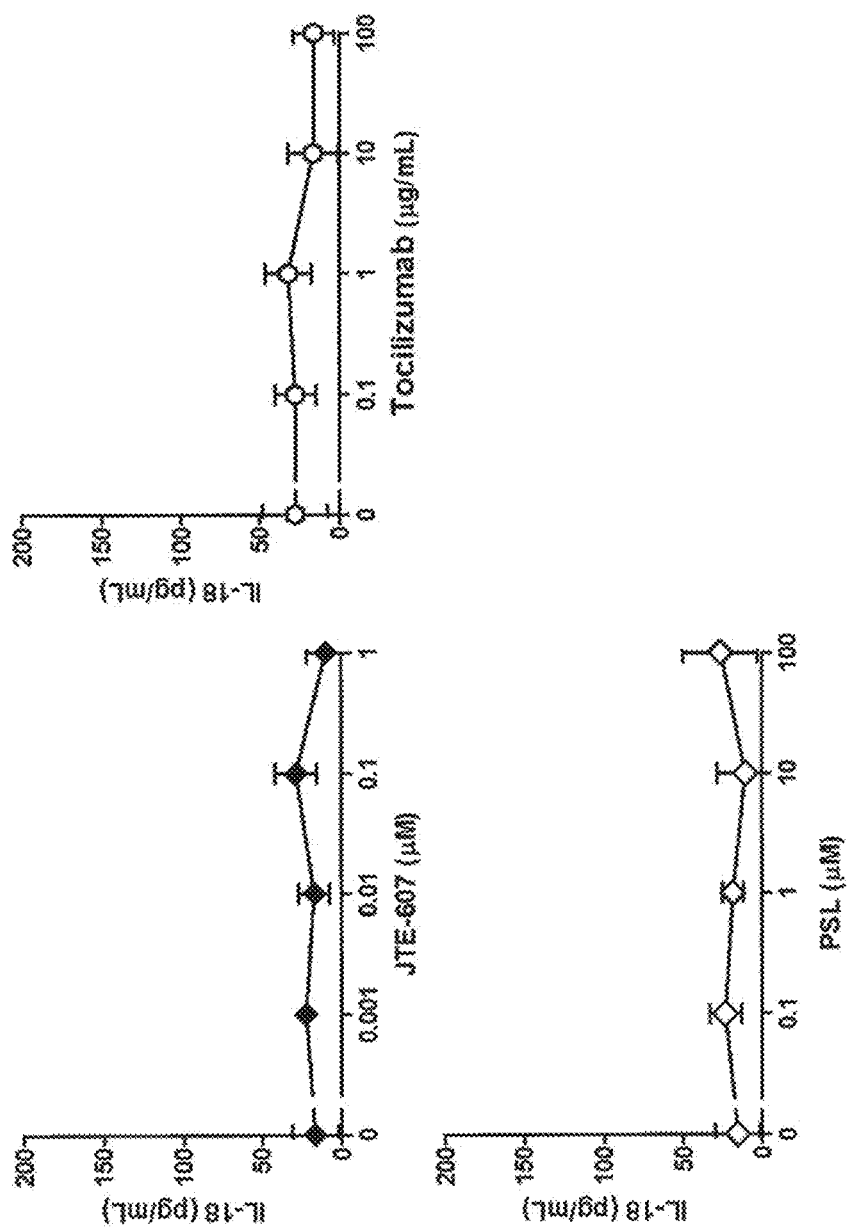
FIG. 25 shows the effects of JTE-607, PSL and tocilizumab on IL-18 production in a CRS toxicity evaluation system using CAR-T cells.

1.3.16 Effects of JTE-607, PSL and Tocilizumab in a CRS Toxicity Evaluation System Using CAR-T Cells The culture supernatants used for killer activity evaluation were evaluated for each cytokine. JTE-607 and PSL were found to have similar suppressive activity on IFN-γ production. JTE-607 had an $IC_{50}$ value of 187.5 nM for IL-6 production. On the other hand, PSL showed no suppressive effect (FIG. 20 and Table 2). JTE-607 showed a concentration-dependent suppressive effect on MCP-1 production and had an $IC_{50}$ value of 37.6 nM. Likewise, PSL had an $IC_{50}$ value of 71.8 μM. On the other hand, tocilizumab showed no suppressive effect (FIG. 21 and Table 2). JTE-607 showed a suppressive effect on IL-8 production and had an $IC_{50}$ value of 153.8 nM. On the other hand, PSL and tocilizumab both showed no suppressive effect (FIG. 22 and Table 2). JTE-607 showed suppressive effects on TNF-α and IL-1β and had $IC_{50}$ values of 413.1 nM for TNF-α and 358.9 nM for IL-1β. On the other hand, PSL and tocilizumab showed no suppressive effect (FIG. 23, FIG. 24 and Table 2). IL-18 was not able to be evaluated because almost no production was observed under the conditions used in this evaluation (FIG. 25 and Table 2).

TABLE 2

Effects ($IC_{50}$ values) of JTE-607, PSL and tocilizumab on various cytokine production in a CRS toxicity evaluation system using CAR-T cells

| Cytokine | JTE-607 | PSL | Tocilizumab |
|---|---|---|---|
| IL-6 | 187.5 nM | >10 μM | — |
| IFN-γ | 598.4 nM | 0.88 μM | — |
| MCP-1 | 37.6 nM | 71.8 μM | >100 μg/mL |
| IL-8 | 153.8 nM | >100 μM | >100 μg/mL |
| TNF-α | 413.1 nM | >100 μM | >100 μg/mL |
| IL-1β | 358.9 nM | >100 μM | >100 μg/mL |
| IL-18 | (870.8 nM) | (>100 μM) | (>100 μg/mL) |

—: Not evaluated
( ): Reference data because of low production

FIG. 26 shows a "schematic diagram illustrating the development of various side effects and symptoms (e.g., irAEs, HLH, MAS) associated with the overactivation of endogenous T effector cells."

T effector cells whose overexpansion is induced, e.g., by immune checkpoint inhibitors and/or virus infection mutually interact with co-existing tissue-resident macrophages and antigen-presenting cells, etc., to cause not only anticancer and antiviral actions but also autoimmune-related adverse events and so on. The immunosuppressive effect of prednisolone (PSL) ameliorates these side effects and symptoms and also entirely inhibits anticancer and antiviral T effector functions.

On the other hand, tocilizumab is used in an attempt to inhibit IL-6 which is overproduced upon macrophage activation, and is expected to reduce and ameliorate autoimmune-related adverse events. JTE-607 is expected to more widely inhibit abnormal macrophage activation and is also shown to cause limited suppression of T effector cells. The discovery underlying the presentation of this diagram is shown in the results obtained for T cell reaction (CD3+ CD28 stimulated reaction system) and monocyte/macrophage reaction (LPS stimulated reaction system) in the single culture system and the combined culture system which is novel.

In view of the foregoing, FIG. 26 shows that JTE-607 is expected to exert the effect of suppressing macrophage activation to ameliorate organ damage without greatly affecting the major functions of T effector cells.

REFERENCE DOCUMENTS

1) JTE-607, a multiple cytokine production inhibitor, induces apoptosis accompanied by an increase in p21waf1/cip1 in acute myelogenous leukemia cells. Tajima N, Fukui K, Uesato N, Maruhashi J, Yoshida T, Watanabe Y, Tojo A. Cancer Sci. 2010 March; 101(3):774-81.
2) CAR T cell-induced cytokine release syndrome is mediated by macrophages and abated by IL-1 blockade. Giavridis T, van der Stegen S J C, Eyquem J, Hamieh M, Piersigilli A, Sadelain M. Nat Med. 2018 June; 24(6):731-738.
3) New drugs, new toxicities: severe side effects of modem targeted and immunotherapy of cancer and their management. Kroschinsky F, Stolzel F, von Bonin S, Beutel G, Kochanek M, Kiehl M, Schellongowski P; Intensive Care in Hematological and Oncological Patients (iCHOP) Collaborative Group. Crit Care. 2017 Apr. 14; 21(1):89.
4) Current concepts in the diagnosis and management of cytokine release syndrome. Lee D W, Gardner R, Porter D L, Louis C U, Ahmed N, Jensen M, Grupp S A, Mackall C L. Blood. 2014 Jul. 10; 124(2):188-95.
5) Severe Cytokine-Release Syndrome after T Cell-Replete Peripheral Blood Haploidentical Donor Transplantation Is Associated with Poor Survival and Anti-IL-6 Therapy Is Safe and Well Tolerated. Abboud R, Keller J, Slade M, DiPersio J F, Westervelt P, Rettig M P, Meier S, Fehniger T A, Abboud C N, Uy G L, Vij R, Trinkaus K M, Schroeder M A, Romee R. Biol Blood Marrow Transplant. 2016 October; 22(10):1851-1860.
6) Kinase inhibitor ibrutinib to prevent cytokine-release syndrome after anti-CD19 chimeric antigen receptor T cells for B-cell neoplasms. bRuella M, Kenderian S S, Shestova O, Klichinsky M, Melenhorst J J, Wasik M A, Lacey S F, June C H, Gill S. Leukemia. 2017 January; 31(1):246-248.
7) A new insight in chimeric antigen receptor-engineered T cells for cancer immunotherapy. Zhang E, Xu H. J Hematol Oncol. 2017 Jan. 3; 10(1):1.
8) A novel chimeric antigen receptor containing a JAK-STAT signaling domain mediates superior antitumor effects. Kagoya Y, Tanaka S, Guo T, Anczurowski M, Wang C H, Saso K, Butler M O, Minden M D, Hirano N. Nat Med. 2018 March; 24(3):352-359.
9) Immuno-oncologic Approaches: CAR-T Cells and Checkpoint Inhibitors. Gay F, D'Agostino M, Giaccone L, Genuardi M, Festuccia M, Boccadoro M, Bruno B. Clin Lymphoma Myeloma Leuk. 2017 August; 17(8):471-478.
10) Varied immuno-related adverse events induced by immune-check point inhibitors—Nivolumab-associated psoriasiform dermatitis related with increased serum level of interleukin-6. Okiyama N, Tanaka R. Nihon Rinsho Meneki Gakkai Kaishi. 2017; 40(2):95-101.
11) Macrophage Activation Syndrome in Patients with Systemic Juvenile Idiopathic Arthritis under Treatment with Tocilizumab. Yokota S, Itoh Y, Morio T, Sumitomo N, Daimaru K, Minota S. J Rheumatol. 2015 April; 42(4):712-22.
12) Hemophagocytic lymphohistiocytosis with immunotherapy: brief review and case report. Sadaat M, Jang S. J Immunother Cancer. 2018 Jun. 5; 6(1):49.
13) Langerhans cell histiocytosis in children: Diagnosis, differential diagnosis, treatment, sequelae, and standardized follow-up. Krooks J, Minkov M, Weatherall A G. J Am Acad Dermatol. 2018 June; 78(6):1047-1056.
14) Chimeric antigen receptor T-cell therapy—assessment and management of toxicities. Neelapu S S, Tummala S, Kebriaei P, Wierda W, Gutierrez C, Locke F L, Komanduri K V, Lin Y, Jain N, Daver N, Westin J, Gulbis A M, Loghin M E, de Groot J F, Adkins S, Davis S E, Rezvani K, Hwu P, Shpall E J. Nat Rev Clin Oncol. 2018 January; 15(1):47-62.
15) Construction and preclinical evaluation of an anti-CD19 chimeric antigen receptor. Kochenderfer J N, Feldman S A, Zhao Y, Xu H, Black M A, Morgan R A, et al. J Immunother. 2009 September; 32(32):689-702.
16) Identification of Predictive Biomarkers for Cytokine Release Syndrome after Chimeric Antigen Receptor T-cell Therapy for Acute Lymphoblastic Leukemia. Teachey D T, Lacey S F, Shaw P A, et al. Cancer Discov. 2016 June; 6(6):664-79.

SEQUENCE LISTING FREE TEXT

SEQ ID NOs: 1 to 6: synthetic DNAs

The invention claimed is:

1. A method for treating or ameliorating cytokine release syndrome (CRS) that does not respond to tocilizumab, wherein the method comprises:
administering to a patient in need thereof an effective amount of a compound represented by the following formula II:

2. The method according to claim 1, wherein the compound represented by formula II or a pharmaceutically acceptable salt thereof is a compound represented by the following formula III:

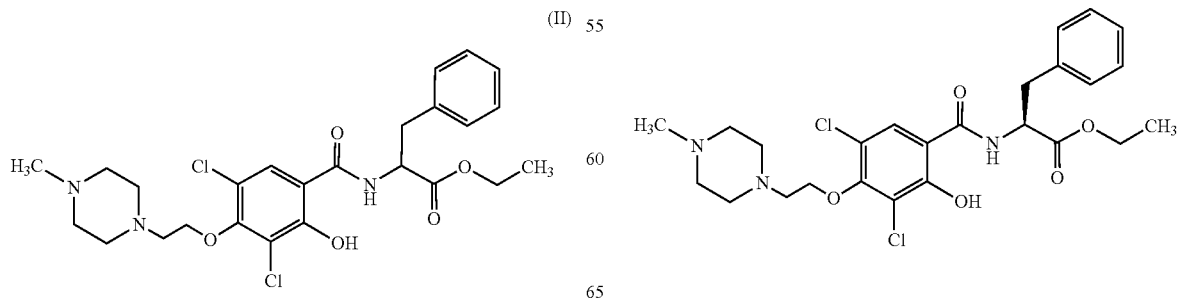

or a pharmaceutically acceptable salt thereof.

or a pharmaceutically acceptable salt thereof.

3. The method according to claim 1, wherein the compound represented by formula II or a pharmaceutically acceptable salt thereof is a hydrochloride salt of the compound represented by formula III.
4. The method according to claim 3, wherein the hydrochloride salt of the compound represented by formula III is a compound represented by the following formula IV:
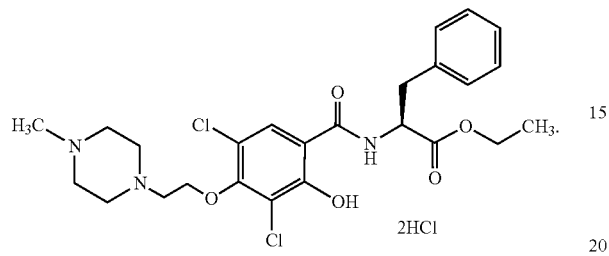
(IV)
2HCl
* * * * *

SEQUENCE LISTING

```
<160> NUMBER OF SEQ ID NOS: 6

<210> SEQ ID NO 1
<211> LENGTH: 35
<212> TYPE: DNA
<213> ORGANISM: Artificial
<220> FEATURE:
<223> OTHER INFORMATION: Synthetic DNA

<400> SEQUENCE: 1
cgctaccgtc gtcgaattcg ccgccaccat gcttc                              35

<210> SEQ ID NO 2
<211> LENGTH: 34
<212> TYPE: DNA
<213> ORGANISM: Artificial
<220> FEATURE:
<223> OTHER INFORMATION: Synthetic DNA
```

```
<400> SEQUENCE: 2
gaagttcgtg ctccgggatc ccgcgagggg gcag                                34

<210> SEQ ID NO 3
<211> LENGTH: 35
<212> TYPE: DNA
<213> ORGANISM: Artificial
<220> FEATURE:
<223> OTHER INFORMATION: Synthetic DNA

<400> SEQUENCE: 3
ccggttcgaa ttcgccatat gccacctccc gcctc                               35

<210> SEQ ID NO 4
<211> LENGTH: 37
<212> TYPE: DNA
<213> ORGANISM: Artificial
<220> FEATURE:
<223> OTHER INFORMATION: Synthetic DNA

<400> SEQUENCE: 4
cgatgttaac tctagatcac ctgggtgctc caggtgc                             37

<210> SEQ ID NO 5
<211> LENGTH: 26
<212> TYPE: DNA
<213> ORGANISM: Artificial
<220> FEATURE:
<223> OTHER INFORMATION: Synthetic DNA

<400> SEQUENCE: 5
gaattcgcca ccatggaaga tgccaa                                         26

<210> SEQ ID NO 6
<211> LENGTH: 24
<212> TYPE: DNA
<213> ORGANISM: Artificial
<220> FEATURE:
<223> OTHER INFORMATION: Synthetic DNA

<400> SEQUENCE: 6
ggatcccacg gcgatcttgc cgcc                                           24
```